US010258305B2

(12) United States Patent
Enomoto et al.

(10) Patent No.: US 10,258,305 B2
(45) Date of Patent: Apr. 16, 2019

(54) RADIOGRAPHIC IMAGE PROCESSING DEVICE, METHOD, AND PROGRAM

(71) Applicant: FUJIFILM Corporation, Tokyo (JP)

(72) Inventors: Jun Enomoto, Kanagawa-ken (JP); Takashi Tajima, Kanagawa-ken (JP); Takeshi Koishi, Kanagawa-ken (JP); Haruyasu Nakatsugawa, Kanagawa-ken (JP); Hirofumi Sawada, Kanagawa-ken (JP); Daiki Harada, Kanagawa-ken (JP); Takahiro Kawamura, Kanagawa-ken (JP); Satoshi Naito, Kanagawa-ken (JP); Hideki Yamagishi, Kanagawa-ken (JP); Noriaki Ida, Kanagawa-ken (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 366 days.

(21) Appl. No.: 15/141,167

(22) Filed: Apr. 28, 2016

(65) Prior Publication Data

US 2016/0235384 A1 Aug. 18, 2016

Related U.S. Application Data

(63) Continuation of application No. PCT/JP2014/005573, filed on Nov. 5, 2014.

(30) Foreign Application Priority Data

Nov. 6, 2013 (JP) .................................. 2013-229943

(51) Int. Cl.
*A61B 6/00* (2006.01)

(52) U.S. Cl.
CPC .......... *A61B 6/5282* (2013.01); *A61B 6/4291* (2013.01); *A61B 6/4464* (2013.01); *A61B 6/5252* (2013.01); *A61B 6/461* (2013.01)

(58) Field of Classification Search
CPC ..... A61B 6/461; A61B 6/4291; A61B 6/5252; A61B 6/5282
See application file for complete search history.

(56) References Cited

U.S. PATENT DOCUMENTS 8,064,676 B2    11/2011  Li et al.
2002/0191829 A1*  12/2002  Sasada .................. H04N 1/393
                                                382/132

(Continued)

FOREIGN PATENT DOCUMENTS

JP    2003-008885 A    1/2003
JP    2003-260053 A    9/2003

(Continued)

OTHER PUBLICATIONS

Communication dated Feb. 28, 2017, from the Japanese Patent Office in counterpart application No. 2013-229943.

(Continued)

*Primary Examiner* — Chih-Cheng Kao
(74) *Attorney, Agent, or Firm* — Sughrue Mion, PLLC

(57) ABSTRACT

It is detected whether a grid stripe is present in a radiographic image. In a case in which the grid stripe is detected, a process of removing the grid stripe from the radiographic image is performed and the radiographic image is displayed. In a case in which the grid stripe is not detected, a process of removing a scattered component from the radiographic image is performed and a radiographic image subjected to the scattered radiation removal process and a radiographic image before the process are displayed.

8 Claims, 14 Drawing Sheets

(56) References Cited

U.S. PATENT DOCUMENTS

| | | | |
|---|---|---|---|
| 2008/0136919 A1* | 6/2008 | Tsuji | H04N 5/232 348/207.1 |
| 2010/0046822 A1* | 2/2010 | Li | A61B 6/00 382/132 |
| 2014/0023252 A1 | 1/2014 | Imai | |

FOREIGN PATENT DOCUMENTS

| | | |
|---|---|---|
| JP | 2006-136741 A | 6/2006 |
| JP | 2010-179092 A | 8/2010 |
| JP | 2012-203504 A | 10/2012 |

OTHER PUBLICATIONS

Christiaan Fivez et al., "Multi-Resolution Contrast Amplification in Digital Radiography With Compensation for Scattered Radiation", IEEE, 1996, pp. 339-342, vol. 1.

John M. Boone et al., "An analytical model of the scattered radiation distribution in diagnostic radiology", Am. Assoc. Phys. Med., Sep./Oct. 1988, pp. 721-726, vol. 15, No. 5.

Written Opinion of PCT/JP2014/005573 dated Mar. 3, 2015.

International Search Report of PCT/JP2014/005573 dated Mar. 3, 2015.

\* cited by examiner

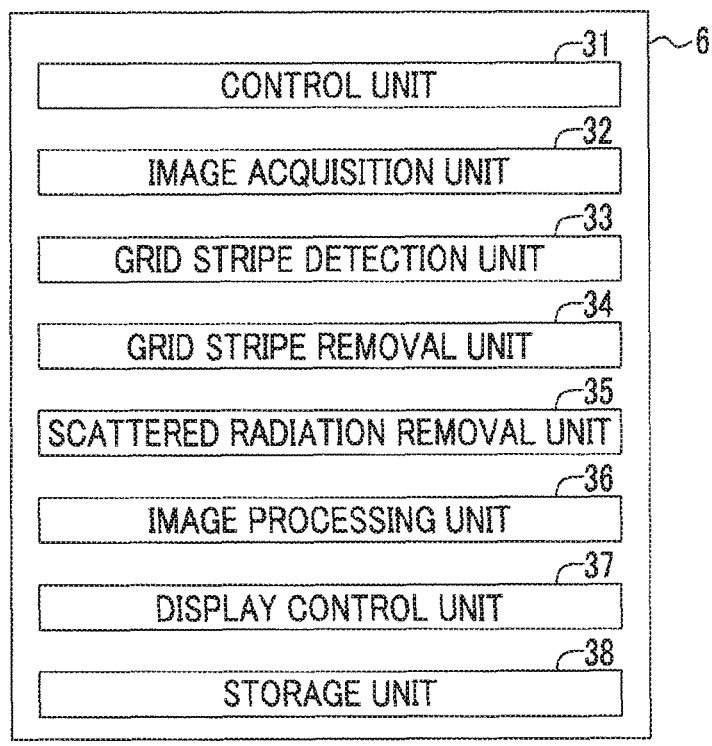
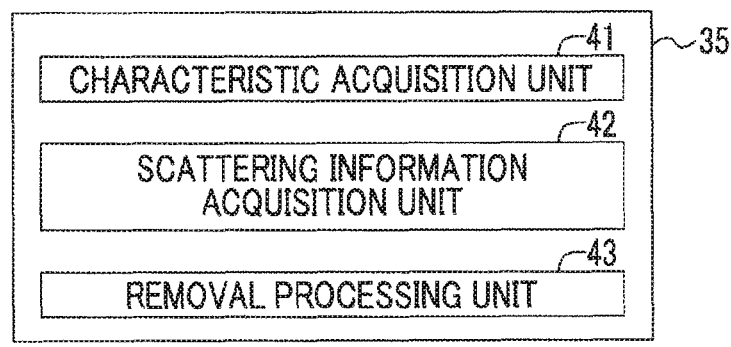

RADIOGRAPHIC IMAGE PROCESSING DEVICE, METHOD, AND PROGRAM

CROSS-REFERENCE TO RELATED APPLICATIONS

This application is a Continuation of PCT International Application No. PCT/JP2014/005573 filed on Nov. 5, 2014, which claims priority under 35 U.S.C. § 119(a) to Japanese Patent Application No. 2013-229943 filed on Nov. 6, 2013. Each of the above applications is hereby expressly incorporated by reference, in its entirety, into the present application.

BACKGROUND OF THE INVENTION

1. Field of the Invention

The present invention relates to a radiographic image processing device and method which performs image processing related to a scattered radiation removal grid for a radiographic image and a program which causes a computer to perform the radiographic image processing method.

2. Description of the Related Art

In the related art, when a radiographic image of a subject is captured using radiation that is transmitted through the subject, the radiation is scattered in the subject and the scattered radiation (hereinafter, also referred to a scattered ray) causes a reduction in the contrast of the acquired radiographic image. For this reason, in some cases, when a radiographic image is captured, a scattered radiation removal grid (hereinafter, simply referred to as a grid) is provided between a subject and a radiation detector which detects radiation and acquires a radiographic image such that the scattered radiation is not emitted to the radiation detector. When imaging is performed using the grid, radiation which is scattered by the subject is less likely to be emitted to the radiation detector. Therefore, the use of the grid makes it possible to improve the contrast of the radiographic image.

In contrast, when imaging is performed using the grid, a subject image and a stripe pattern (grid strips) corresponding to the grid are included in the radiographic image, which makes it difficult to see the image. For this reason, a process is known which removes grid stripes from a radiographic image (see JP2012-203504A). In addition, the grid stripes are generated in a case in which a stationary grid is used for imaging in a stationary state and is not generated from a radiographic image in a case in which an oscillating grid (Bucky grid) oscillates and is then used. Therefore, it is possible to acquire a high-quality radiographic image without a grid stripe, without performing the grid stripe removal process.

The grid has a structure in which radiopaque lead and a radiolucent interspace material, such as aluminum or fiber, are alternately arranged with a fine grid density of, for example, about 4.0 lines/mm. Therefore, the grid is weighty. For this reason, in portable radiography which is performed in, for example, a hospital room, the grid needs to be provided between a lying patent and a radiation detector and the weight of the grid causes an increase in the burden of an arrangement operation on a radiographer and an increase in strain on the patient during imaging. Further, in the case of a convergence-type grid, density unevenness is likely to occur in the radiographic image due to the oblique incidence of radiation.

For this reason, a process has been proposed which captures a radiographic image, without using a grid, and gives an image quality improvement effect, which can be obtained by removing scattered radiation using a grid, to the radiographic image through image processing (see U.S. Pat. No. 8,064,676B and C. Fivez et al., Multi-resolution contrast amplification in digital radiography with compensation for scattered radiation, 1996 IEEE, pp. 339-342). The methods described in U.S. Pat. No. 8,064,676B and C. Fivez et al., "Multi-resolution contrast amplification in digital radiography with compensation for scattered radiation", 1996 IEEE, pp. 339-342 decompose a radiographic image into a plurality of frequency components, perform a scattered radiation removal process of controlling contrast or latitude for a low-frequency component which is regarded as a scattered radiation component, and combine the processed frequency components to acquire a radiographic image from which the scattered radiation component has been removed. In the method described in U.S. Pat. No. 8,064,676B, the scattered radiation removal process is performed by multiplying a low-frequency component by a gain corresponding to the hierarchy of the low-frequency component and the pixel value of the low-frequency component. Here, the gain is less than 1. The gain has a smaller value in a lower frequency band and is reduced as the pixel value increases. The method described in C. Fivez et al., "Multi-resolution contrast amplification in digital radiography with compensation for scattered radiation", 1996 IEEE, pp. 339-342 uses a table for converting a low-frequency component according to the pixel value thereof. In the method, lower frequency bands are increasingly reduced in a geometric progression manner.

According to the methods described in U.S. Pat. No. 8,064,676B and C. Fivez et al., "Multi-resolution contrast amplification in digital radiography with compensation for scattered radiation", 1996 IEEE, pp. 339-342, since no grid is required during imaging, it is possible to reduce strain on a patient during imaging and to prevent the deterioration of image quality due to density unevenness and a grid stripe.

In contrast, a general radiography system acquires three types of radiographic image, that is, a radiographic image which is captured using a stationary grid, a radiographic image which is captured using a Bucky grid, and a radiographic image which is captured without using a grid. In this situation, in a case in which a grid stripe removal process is performed for the acquired radiographic images, the grid stripe removal process is also performed for the radiographic image which is captured without using a grid. Inversely, in a case in which a scattered radiation removal process is performed, the scattered radiation removal process is also performed for the radiographic image which is captured using a grid. As such, when a process which is not necessary for the radiographic image is performed for the radiographic image, the quality of the radiographic image deteriorates significantly, which makes it difficult to make a diagnosis with high efficiency.

For this reason, a method has been proposed which detects whether a grid is present and the type of grid, on the basis of, for example, the weight of the grid or projections that are formed on the grid according to the types of microswitch and grid, and performs image processing corresponding to whether a grid is present and the type of grid, in systems that use a grid, do not use a grid, and use a plurality of types of grid (see JP2003-260053A). In particular, JP2003-260053A discloses a method which selects whether to perform a grid stripe removal process on the basis of information indicating whether a grid is present.

SUMMARY OF THE INVENTION

In the method disclosed in JP2003-260053A, it is necessary to provide means for measuring the weight of the microswitch and the grid in the system, which results in an increase in the size of the system. For this reason, a structure is considered which enables an operator to check a radiographic image and to perform a necessary process. However, this structure in which the operator needs to check the radiographic image causes an increase in burden on the operator. In particular, in a case in which a radiographic image is captured using the Bucky grid, no grid stripe is included in the acquired radiographic image. Therefore, there is a concern that the scattered radiation removal process will be performed even if the operator checks the process.

The invention has been made in view of the above-mentioned problems and an object of the invention is to provide a technique which performs a grid stripe removal process and a scattered radiation removal process with high efficiency, according to whether a grid is used during imaging, while reducing a burden on a radiographer.

According to the invention, there is provided a radiographic image processing device comprising: image acquisition means for acquiring a radiographic image which is captured by irradiating a subject with radiation; grid stripe detection means for detecting whether a grid stripe, which is a stripe pattern caused by a grid used during imaging, is present in the radiographic image; grid stripe removal means for performing a grid stripe removal process for the radiographic image in a case in which the grid stripe is detected; scattered radiation removal means for performing a scattered radiation removal process of removing a scattered component included in the radiation that is transmitted through the subject during imaging from the radiographic image in a case in which the grid stripe is not detected; and display control means for displaying a radiographic image subjected to the grid stripe removal process on display means in the case in which the grid stripe is detected and displaying a radiographic image subjected to the scattered radiation removal process and a radiographic image before the scattered radiation removal process on the display means in the case in which the grid stripe is not detected.

The "grid stripe which is a stripe pattern caused by a grid used during imaging" includes a periodic stripe which is caused by the period of the grid and moire which is caused by the periodic stripes and occurs due to the sampling of a radiographic image.

The "grid removal process" means a process which removes a stripe pattern caused by the grid from the radiographic image.

The radiographic image processing device according to the invention may further comprise control means for deleting the radiographic image before the scattered radiation removal process in response to an operation of an operator in the case in which the grid stripe is not detected.

In this case, the operation of the operator may be an image decision operation which is performed after the radiographic image is checked.

The "image decision operation" is the operation of the operator confirming that a target part of the subject does not need to be captured again after the operator checks the displayed image.

The radiographic image processing device according to the invention may further comprise storage means for storing the radiographic image subjected to the scattered radiation removal process and the radiographic image before the scattered radiation removal process in the case in which the grid stripe is not detected and deleting the radiographic image before the scattered radiation removal process after a predetermined period of time has elapsed.

The radiographic image processing device according to the invention may further comprise scattered radiation dose estimation means for estimating a scattered radiation dose of the radiographic image in the case in which the grid stripe is not detected and determination means for determining whether the grid has been used on the basis of the scattered radiation dose. The scattered radiation removal processing means may perform the scattered radiation removal process in a case in which it is determined that the grid has not been used.

The radiographic image processing device according to the invention may further comprise scattered radiation dose estimation means for estimating a scattered radiation dose of the radiographic image in the case in which the grid stripe is not detected and determination means for determining whether the grid has been used on the basis of the scattered radiation dose. The display control means may determine which of the radiographic image subjected to the scattered radiation removal process and the radiographic image before the scattered radiation removal process is displayed, on the basis of the determination result.

According to the invention, there is provided a radiographic image processing method that is performed by a computer. The radiographic image processing method comprises: acquiring a radiographic image which is captured by irradiating a subject with radiation; detecting whether a grid stripe, which is a stripe pattern caused by a grid used during imaging, is present in the radiographic image; performing a grid stripe removal process for the radiographic image in a case in which the grid stripe is detected; performing a scattered radiation removal process of removing a scattered component included in the radiation that is transmitted through the subject during imaging from the radiographic image in a case in which the grid stripe is not detected; and displaying a radiographic image subjected to the grid stripe removal process on display means in the case in which the grid stripe is detected and displaying a radiographic image subjected to the scattered radiation removal process and a radiographic image before the scattered radiation removal process on the display means in the case in which the grid stripe is not detected.

In addition, a radiographic image processing program may be provided that causes a computer to perform the radiographic image processing method according to the invention.

According to the invention, it is detected whether a grid stripe, which is a stripe pattern caused by a grid used during imaging, is present in a radiographic image. In a case in which the grid stripe is detected, the grid stripe removal process is performed. In a case in which the grid stripe is not detected, the scattered radiation removal process is performed. In the case in which the grid stripe is detected, a radiographic image subjected to the grid stripe removal process is displayed on the display means. In the case in which the grid stripe is not detected, the radiographic image subjected to the scattered radiation removal process and a radiographic image before the scattered radiation removal process are displayed on the display means. Therefore, when the operator does not perform any operation, it is possible to perform an appropriate process corresponding to whether the grid has been used during imaging for the radiographic image. As a result, it is possible to reduce a burden on the operator and to perform the grid stripe removal process and the scattered radiation removal process with high efficiency.

In a case in which the Bucky grid is used, no grid stripe is detected from the radiographic image. Therefore, the scattered radiation removal process is performed. Scattered radiation has been removed from the radiographic image which is captured using the Bucky grid. Therefore, when the scattered radiation removal process is further performed for the radiographic image, an image with a large amount of noise which seems to be captured with an excessively low dose is obtained. According to the invention, the radiographic image subjected to the scattered radiation removal process and the radiographic image before the scattered radiation removal process are displayed. Therefore, the operator can check whether the displayed image is obtained by performing the scattered radiation removal process for the radiographic image captured using the Bucky grid and can perform, for example, a process of deleting an image which is obtained by performing the scattered radiation removal process for the radiographic image captured using the Bucky grid. As a result, it is possible to prevent a radiographic image, which is obtained by performing the scattered radiation removal process for the radiographic image captured using the Bucky grid, from remaining and from being used for diagnosis.

In a case in which the grid stripe is not detected, the operator deletes the radiographic image before the scattered radiation removal process. Therefore, it is possible to prevent a radiographic image, which is obtained by performing the scattered radiation removal process for the radiographic image captured using the Bucky grid, from remaining and from being used for diagnosis.

In a case in which the grid stripe is not detected, the radiographic image subjected to the scattered radiation removal process and the radiographic image before the scattered radiation removal process are stored. The radiographic image before the scattered radiation removal process is deleted after a predetermined period of time has elapsed. Therefore, it is possible to reliably prevent a radiographic image, which is obtained by performing the scattered radiation removal process for the radiographic image captured using the Bucky grid, from remaining and from being used for diagnosis.

In addition, the scattered radiation dose of the radiographic image is estimated and it is determined whether a grid has been used on the basis of the scattered radiation dose. In a case in which it is determined that the grid has not been used, the scattered radiation removal process is performed. The scattered radiation removal process is not performed in a case in which a low scattered radiation dose is included in the radiographic image as in a case in which the Bucky grid is used. Therefore, it is possible to prevent the scattered radiation removal process from being performed for the radiographic image captured using the Bucky grid.

Furthermore, the scattered radiation dose of the radiographic image is estimated and it is determined whether a grid has been used on the basis of the scattered radiation dose. It is determined which of the radiographic image subjected to the scattered radiation removal process and the radiographic image before the scattered radiation removal process is displayed, on the basis of the determination result. Therefore, it is possible to display only the radiographic image which has not been subjected to the scattered radiation removal process in a case in which a low scattered radiation dose is included in the radiographic image as in a case in which the Bucky grid is used.

BRIEF DESCRIPTION OF THE DRAWINGS

FIG. 2 is a block diagram schematically illustrating the internal structure of a computer of the radiography system in the first embodiment.

FIG. 3 is a block diagram schematically illustrating the structure of a scattered radiation removal unit.

DESCRIPTION OF THE PREFERRED EMBODIMENTS

Figure 1:
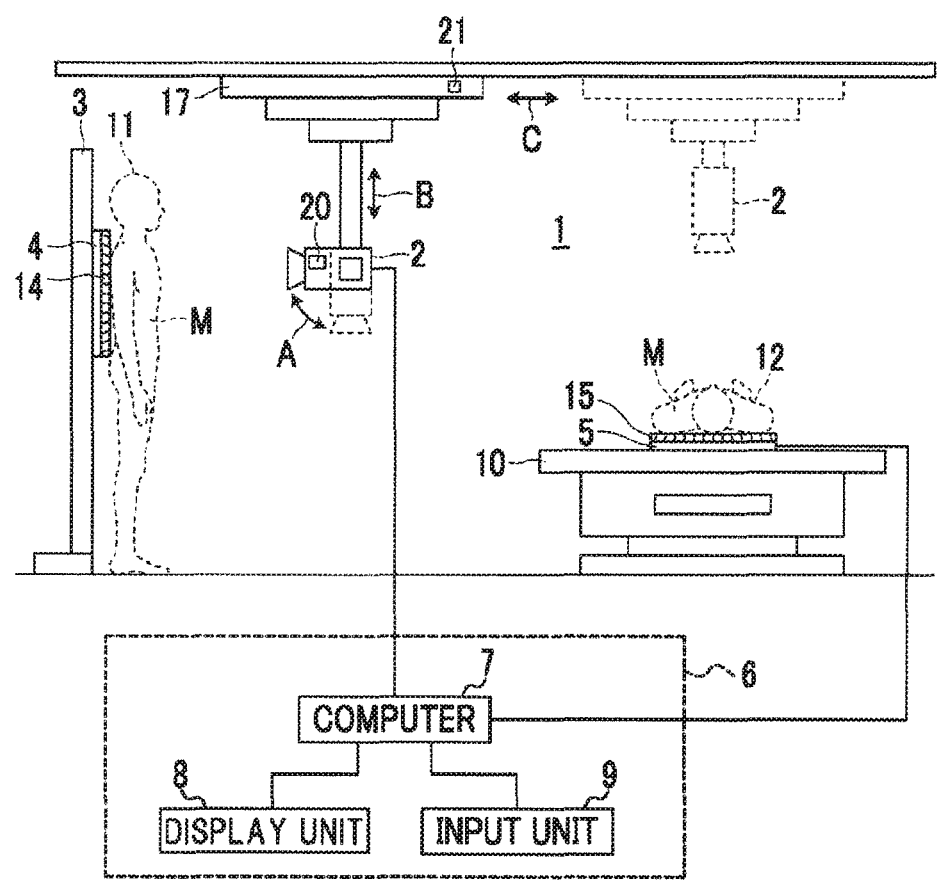
FIG. 1 is a block diagram schematically illustrating the structure of a radiography system to which a radiographic image processing device according to a first embodiment of the invention is applied.

Hereinafter, embodiments of the invention will be described with reference to the drawings. FIG. 1 is a block diagram schematically illustrating the structure of a radiography system to which a radiographic image processing device according to a first embodiment of the invention is applied. As illustrated in FIG. 1, the radiography system according to this embodiment includes a radiation source 2, a radiation detector 4 which is held by a rack (upright radiographic stand) 3, a radiation detector 5 for capturing a radiographic image at a free position, and a console 6 for controlling the system. The console 6 includes a computer 7 and a display unit 8 and an input unit 9 which are connected to the computer 7. FIG. 1 illustrates a state in which the radiation detector 5 is provided in a bed (decubitus radiographic stand) 10 on which a subject M, who is a patient, lies. In addition, a space in front of the rack 3 is an imaging position 11 of the subject M when radiography is performed in the upright position and a space above the bed 10 is an imaging position 12 of the subject M when radiography is performed in the decubitus position.

In addition, grids 14 and 15 which prevent radiation scattered in the subject M from being incident on the radiation detectors 4 and 5 are removably provided on the subject side of the radiation detectors 4 and 5. In this embodiment, the grid 14 is a swingable Bucky grid and the grid 15 is a stationary grid.

A radiography room 1 is provided with a support and movement mechanism 17 which can rotate the radiation source 2 on a horizontal axis (the direction of an arrow A in FIG. 2), move the radiation source 2 in the vertical direction (the direction of an arrow B in FIG. 2), and move the radiation source 2 in the horizontal direction (the direction of an arrow C in FIG. 2), in order to perform radiography in both the upright position and the decubitus position with radiation from the single radiation source 2.

The support and movement mechanism 17 includes a driving source that rotates the radiation source 2 on the horizontal axis, a driving source that moves the radiation source 2 in the vertical direction, and a driving source that moves the radiation source 2 in the horizontal direction. The radiation source 2 and the support and movement mechanism 17 are driven by a radiation controller 20 which is provided in the radiation source 2 and a driving controller 21, respectively.

Each of the radiation detectors 4 and 5 can repeatedly perform a process of recording and reading a radiographic image and may be a so-called direct radiation detector which directly receives radiation and generates charge or a so-called indirect radiation detector which converts radiation into visible light and converts the visible light into a charge signal. In addition, as a method for reading a radiographic image signal, it is preferable to use a so-called a TFT reading method which turns on and off a thin film transistor (TFT) switch to read a radiographic image signal or a so-called optical reading method which emits reading light to read a radiographic image signal. However, the invention is not limited thereto. Other methods may be used.

The radiation detector 4 is located at a predetermined position of the rack 3. The radiation detector 5 can be installed at a free position and then used. The reading of charge signals from the radiation detectors 4 and 5 is performed in response to an instruction from the console 6.

In the radiography system according to this embodiment, the radiation source 2 and the support and movement mechanism 17 are connected to the console 6 by a cable and various kinds of information are transmitted and received therebetween by wired communication. In this embodiment, the radiation detectors 4 and 5 and the console 6 transmit and receive various kinds of information therebetween through the cable, using wired communication. However, the radiation detectors 4 and 5 and the console 6 may transmit and receive various kinds of information therebetween, using wireless communication.

The computer 7 of the console 6 includes, for example, a central processing unit (CPU), a semiconductor memory, a communication interface, and a storage device, such as a hard disk or an SSD. A control unit 31, an image acquisition unit 32, a grid stripe detection unit 33, a grid stripe removal unit 34, a scattered radiation removal unit 35, an image processing unit 36, a display control unit 37, and a storage unit 38 illustrated in FIG. 2 are implemented by these hardware components. In addition, the control unit 31, the image acquisition unit 32, the grid stripe detection unit 33, the grid stripe removal unit 34, the scattered radiation removal unit 35, the display control unit 37, and the storage unit 38 form the radiographic image processing device according to the invention.

The control unit 31 outputs a predetermined control signal to various types of controllers 20 and 21 to control these controllers, or controls the overall operation of the system.

The image acquisition unit 32 reads the charge signals from the radiation detectors 4 and 5 and acquires a radiographic image of the subject M. In addition, the image acquisition unit 32 is provided with, for example, a circuit board including a charge amplifier which converts the charge signals read from the radiation detectors 4 and 5 into voltage signals, a correlated double sampling circuit which samples the voltage signal output from the charge amplifier, and an A/D converter which converts the voltage signal into a digital signal.

The grid stripe detection unit 33 detects whether there is a grid stripe, which is a stripe pattern caused by a grid used during imaging, in a radiographic image. Specifically, the grid stripe detection unit 33 performs frequency analysis for a radiographic image to calculate a frequency spectrum and determines whether a peak is present in a certain frequency component in the frequency spectrum. Here, a radiographic image which is acquired by an imaging process using the grid includes a periodic stripe caused by the period of the grid and moire which is caused by the periodic stripe and occurs due to the sampling of a radiographic image. Therefore, there is a peak in a frequency component corresponding to the period of the grid and moire in the frequency spectrum. Therefore, the grid stripe detection unit 33 determines whether there is a peak in the calculated frequency spectrum and detects whether there is a grid stripe in the radiographic image on the basis of the determination result.

In a case in which the grid stripe detection unit 33 detects a grid stripe in the radiographic image, the grid stripe removal unit 34 performs a grid stripe removal process of removing the grid stripe from the radiographic image. For example, a filtering process using a filter for reducing a frequency component corresponding to a grid stripe can be used as the grid stripe removal process.

In a case in which the grid stripe detection unit 33 does not detect a grid stripe in the radiographic image, the scattered radiation removal unit 35 performs a scattered radiation removal process of removing scattered radiations from the radiographic image. FIG. 3 is a block diagram schematically illustrating the structure of the scattered radiation removal unit. As illustrated in FIG. 3, the scattered radiation removal unit 35 includes a characteristic acquisition unit 41 that acquires virtual grid characteristics, which are the characteristics of a virtual grid, a scattering information acquisition unit 42 that acquires scattered component information indicating a scattered component of radiation included in the radiographic image, and a removal processing unit 43 that performs the scattered radiation removal process for the radiographic image acquired by the radiation detector 4 and 5, on the basis of the virtual grid characteristics acquired by the characteristic acquisition unit 41 and the scattered component information acquired by the scattering information acquisition unit 42, which are assumed to be used in order to remove scattered radiations when a radiographic image is captured.

The characteristic acquisition unit 41 acquires the virtual grid characteristics which are input from an operator through the input unit 9. In this embodiment, it is assumed that the virtual grid characteristics include scattered radiation transmittance $T_s$ for the virtual grid and the transmittance (primary radiation transmittance) $T_p$ of primary radiation which passes through the subject M and is directly emitted to the radiation detectors 4 and 5. In addition, it is assumed that the values of the scattered radiation transmittance $T_s$ and the primary radiation transmittance $T_p$ are in the range of 0 to 1.

The characteristic acquisition unit 41 may directly receive the values of the scattered radiation transmittance Ts and the primary radiation transmittance Tp to acquire the virtual grid characteristics. In this embodiment, the characteristic acquisition unit 41 receives the designation of at least one of grid information indicating the type of grid, information about the subject (subject information), or imaging conditions when a radiographic image is acquired and acquires the virtual grid characteristics, that is, the scattered radiation transmittance Ts and the primary radiation transmittance Tp.

Here, the grid information includes at least one of information items for specifying the type of grid, such as a grid ratio, grid density, information indicating whether the grid is a convergence type or a parallel type, a focusing distance in a case in which the grid is a convergence type, and an interspace material (for example, aluminum, fiber, or Bakelite). The scattered radiation transmittance Ts and the primary radiation transmittance Tp vary depending on the type of grid. Therefore, for the grid information, a table in which at least one of various kinds of grid information is associated with the virtual grid characteristic is stored in the storage unit 38.

The subject information includes the type of subject, such as the chest, the abdomen, and the head. When a radiographic image is captured, in general, the type of grid to be used is determined according to the part of which the image is to be captured. The scattered radiation transmittance Ts and the primary radiation transmittance Tp vary depending on the type of grid. Therefore, for the subject information, a table in which various kinds of subject information are associated with the virtual grid characteristic is stored in the storage unit 38.

The imaging conditions include at least one of a source-image receptor distance (SID) during imaging, an imaging dose, a tube voltage, a target of a radiation source, a material forming a filter, or the type of radiation detector used for imaging. In general, when a radiographic image is captured, the type of grid to be used is determined according to the imaging conditions and the scattered radiation transmittance Ts and the primary radiation transmittance Tp vary depending on the type of grid. Therefore, for the imaging conditions, a table in which various imaging conditions are associated with the virtual grid characteristic is stored in the storage unit 38. In many cases, various imaging conditions are determined according to facilities in which the radiography system is installed. Therefore, in a case in which the imaging conditions during actual imaging are unclear, the imaging conditions corresponding to facilities may be used.

The characteristic acquisition unit 41 acquires the virtual grid characteristic on the basis of at least one of the grid information, the subject information, or the imaging conditions input from the input unit 9, with reference to the tables stored in the storage unit 38. The grid information, the subject information, and the imaging conditions may be directly received through the input unit 9. Alternatively, a list of various kinds of grid information, various kinds of subject information, and various imaging conditions may be displayed on the display unit 8, and the grid information, the subject information, and the imaging conditions may be received when the operator selects at least one of the grid information, the subject information, or the imaging conditions from the list. The imaging conditions may be acquired from the radiation controller 20.

In a case in which the imaging condition is an imaging dose, the radiographic image of an acrylic model having a known thickness may be captured together with the radiographic image of the subject and the imaging dose may be acquired on the basis of the concentration of the acrylic model in the acquired radiographic image. In this case, a table in which the concentration of the acrylic model is associated with the imaging dose may be stored in the storage unit 38 and the imaging dose may be acquired on the basis of the concentration of the acrylic model, with reference to the table. In a case in which a void region that is obtained by the direct emission of radiation to the radiation detectors 4 and 5 is included in the radiographic image, the imaging dose may be acquired on the basis of the concentration of the void region. In this case, a table in which the concentration of the void region is associated with the imaging dose may be stored in the storage unit 38 and the imaging dose may be acquired on the basis of the concentration of the void region, with reference to the table. The imaging dose may be measured using a dosimeter, and the measured imaging dose may be used as the imaging condition.

In this embodiment, the scattered radiation removal process is performed by performing frequency decomposition for the radiographic image, which will be described below. In this embodiment, the virtual grid characteristics are acquired for each of a plurality of frequency bands of the radiographic image obtained by frequency decomposition. Therefore, the virtual grid characteristics are associated with each of the plurality of frequency bands in the above-mentioned table.

In addition, a table in which all of the grid information, the subject information, and the imaging conditions are associated with the virtual grid characteristic may be stored in the storage unit 38 and the virtual grid characteristic may be acquired on the basis of all of the grid information, the subject information, and the imaging conditions. In this case, the table is at least a four-dimensional table in which various kinds of grid information, various kinds of subject information, and various imaging conditions are associated with the virtual grid characteristics.

An exposure magnification factor which is the rate of increase in an irradiation dose due to the use of the grid, a contrast improvement coefficient which is the ratio of contrast in a case in which the grid is used and in a case in which the grid is not used, and selectivity which is the ratio of primary X-ray transmittance to scattered X-ray transmittance are characteristic values indicating the characteristic of the grid. The scattered radiation transmittance Ts and the primary radiation transmittance Tp can be calculated from the characteristic values. Therefore, the characteristic acquisition unit 41 may receive the designation of at least one of the exposure magnification factor, the contrast improvement coefficient, or the selectivity, calculate the virtual grid characteristics, that is, the scattered radiation transmittance Ts and the primary radiation transmittance Tp, and acquire the virtual grid characteristics.

In this embodiment, the scattered radiation removal unit 35 performs the scattered radiation removal process on the basis of the scattered component information, in addition to the virtual grid characteristics. Therefore, the scattering information acquisition unit 42 acquires the scattered component information. In this embodiment, it is assumed that the scattered component information is a scattered radiation content distribution in the radiographic image. In the scattered radiation content distribution, for example, if the subject M is the chest, the amount of scattered radiation increases toward the center of the radiographic image at which a mediastinal part is present and the amount of scattered radiation decreases toward the periphery of the radiographic image in which the lung field is present.

The scattering information acquisition unit 42 analyzes the captured radiographic image to acquire the scattered component information, that is, the scattered radiation content distribution. The radiographic image is analyzed on the basis of irradiation field information, the subject information, and the imaging conditions when the radiographic image is captured.

The irradiation field information is information indicating an irradiation field distribution related to the position and size of the irradiation field which is included in the radiographic image when imaging is performed using an irradiation field diaphragm. The subject information is information related to, for example, the position of the subject on the radiographic image, the distribution of the composition of the subject, the size of the subject, and the thickness of the subject, in addition to the type of subject, such as the chest, the abdomen, or the head. The imaging conditions are information related to, for example, an imaging dose (tube current×irradiation time) during imaging, a tube voltage, a source-image receptor distance (the sum of the distance from the radiation source to the subject and the distance from the subject to the radiation detector), an air gap (the distance from the subject to the radiation detector), and the characteristics of the radiation detector. The irradiation field information, the subject information, and the imaging conditions are factors for determining the distribution of the scattered radiations included in the radiographic image. For example, the amount of scattered radiations depends on the magnitude of the irradiation field. As the thickness of the subject increases, the amount of scattered radiations increases. If there is air between the subject and the radiation detector, the amount of scattered radiations decreases. Therefore, the use of these information items makes it possible to accurately acquire the scattered radiation content distribution.

The scattering information acquisition unit 42 calculates a primary radiation image and a scattered radiation image from the distribution $T(x, y)$ of the thickness of the subject in the captured radiographic image, on the basis of the following Expressions (1) and (2), and calculates a scattered radiation content distribution $S(x, y)$ from the calculated primary radiation image and scattered radiation image, on the basis of Expression (3). The scattered radiation content distribution $S(x, y)$ has a value of 0 to 1.

$$Icp(x,y)=Io(x,y)\times\exp(-\mu\times T(x,y)) \quad (1)$$

$$Ics(x,y)=Io(x,y)*S\sigma(T(x,y)) \quad (2)$$

$$S(x,y)=Ics(x,y)/(Ics(x,y)+Icp(x,y)) \quad (3)$$

Here, $(x, y)$ is the coordinates of a pixel position in a radiographic image, $Icp(x, y)$ is a primary radiation image at the pixel position $(x, y)$, $Ics(x, y)$ is a scattered radiation image at the pixel position $(x, y)$, $Io(x, y)$ is an incident dose on the surface of the subject at the pixel position $(x, y)$, $\mu$ is a linear attenuation coefficient of the subject, and $S\sigma(T(x, y))$ is a convolution kernel indicating scattering characteristics corresponding to the thickness of the subject at the pixel position $(x, y)$. Expression (1) is based on a known exponential attenuation rule and Expression (2) is based on the method described in "J M Boon et al., An analytical model of the scattered radiation distribution in diagnostic radiolog, Med. Phys. 15(5), September/October 1988" (Reference Document 1). Even if the incident dose $Io(x, y)$ on the surface of the subject is defined as any value, the incident dose $Io(x, y)$ is cancelled by division when $S(x, y)$ is calculated. Therefore, the incident dose $Io(x, y)$ may be set to an arbitrary value, for example, 1.

The distribution $T(x, y)$ of the thickness of the subject may be calculated by converting the pixel value of the radiographic image into a thickness, using the linear attenuation coefficient, on the assumption that a brightness distribution in the radiographic image is substantially identical to the distribution of the thickness of the subject. Alternatively, the thickness of the subject may be measured using, for example, a sensor or may be approximated by a model, such as a cube or an elliptic cylinder.

In Expression (2), * is an operator indicating a convolution operation. The properties of a kernel change depending on, for example, the distribution of the irradiation field, the distribution of the composition of the subject, the irradiation dose during imaging, the tube voltage, the source-image receptor distance, the air gap, and the characteristics of the radiation detector, in addition to the thickness of the subject. According to the method described in Reference Document 1, scattered radiation can be approximated by the convolution of a point spread function ($S\sigma(T(x, y))$ in Expression (2)) with respect to the primary radiation.

In addition, $S\sigma(T(x, y))$ can be experimentally calculated on the basis of, for example, the irradiation field information, the subject information, the imaging conditions.

In this embodiment. $S\sigma(T(x, y))$ may be calculated on the basis of the irradiation field information, the subject information, and the imaging conditions during imaging. A table in which various kinds of irradiation field information, various kinds of subject information, and various imaging conditions are associated with $S\sigma(T(x, y))$ may be stored in the storage unit 38 and $S\sigma(T(x, y))$ may be calculated on the basis of the irradiation field information, the subject information, and the imaging conditions during imaging, with reference to the table. In addition, $S\sigma(T(x, y))$ may be approximated by $T(x, y)$.

The removal processing unit 43 reduces a frequency component in a frequency band which is regarded as scattered radiation in the radiographic image, on the basis of the virtual grid characteristics and the scattered component information, thereby performing the scattered radiation removal process. The removal processing unit 43 performs frequency decomposition for the radiographic image to acquire frequency components for a plurality of frequency bands, reduces the gain of at least one frequency component, and synthesizes the processed frequency component and the other frequency components to acquire a radiographic image subjected to the scattered radiation removal process. As a frequency decomposition method, in addition to a method for performing multi-resolution conversion for the radiographic image, other known methods, such as wavelet transform and Fourier transform, can be used.

The removal processing unit 43 calculates a conversion coefficient $R(x, y)$ for converting a frequency component from the scattered radiation transmittance Ts and the primary radiation transmittance Tp, which are the virtual grid characteristic, and the scattered radiation content distribution $S(x, y)$, using the following Expression (4).

$$R(x,y)=S(x,y)\times Ts+(1-S(x,y))\times Tp \quad (4)$$

Since each of the scattered radiation transmittance Ts, the primary radiation transmittance Tp, and the scattered radiation content distribution $S(x, y)$ has a value of 0 to 1, the conversion coefficient $R(x, y)$ also has a value of 0 to 1. The removal processing unit 43 calculates the conversion coefficient $R(x, y)$ for each of a plurality of frequency bands.

In the following description, it is assumed that the pixel value of a radiographic image is represented by I(x, y), a frequency component image obtained by frequency decomposition is represented by I(x, y, r), frequency synthesis is represented by I(x, y)=Σrl(x, y, r), a conversion coefficient for each frequency band is represented by R(x, y, r), and the scattered radiation transmittance and the primary radiation transmittance of each frequency band are represented by Ts(r) and Tp(r), respectively. In addition, "r" indicates the layer of a frequency band. As r becomes greater, the frequency becomes lower. Therefore, I(x, y, r) indicates a frequency component image of a certain frequency band. The scattered radiation content distribution S(x, y) for the radiographic image may be used without any change, or may be acquired for each frequency band, similarly to the scattered radiation transmittance Ts and the primary radiation transmittance Tp.

In this embodiment, the conversion coefficient R(x, y, r) is calculated for each frequency component and the frequency component image I(x, y, r) is multiplied by the conversion coefficient R(x, y, r) of the corresponding frequency band to convert the pixel value of the frequency component image I(x, y, r). Then, frequency synthesis is performed for the frequency component image I(x, y, r) multiplied by the conversion coefficient R(x, y, r) (that is, I(x, y, r)×R(x, y, r)) to acquire a processed radiographic image I'(x, y). Therefore, the process which is performed by the removal processing unit 43 is represented by the following Expression (5). Since the conversion coefficient R(x, y, r) has a value of 0 to 1, the pixel value of the frequency component at the pixel position (x, y), that is, the gain is reduced by multiplying the frequency component (x, y, r) by the conversion coefficient R(x, y, r) of the corresponding frequency band.

$$I'(x, y) = \Sigma r\{I(x, y, r) \times R(x, y, r)\} = \qquad (5)$$
$$\Sigma r\{I(x, y, r) \times (S(x, y) \times Ts(r) + (1 - S(x, y)) \times Tp(r))\}$$

In this embodiment, it is assumed that the radiographic image is decomposed into six frequency bands and the scattered radiation transmittance Ts and the primary radiation transmittance Tp are acquired for the six frequency bands. In this case, the scattered radiation transmittance Ts and the primary radiation transmittance Tp have, for example, values shown in the following Expression (6). In Expression (6), it is assumed that a value closer to the right side indicates a lower frequency band.

$$Ts=\{0.7, 0.7, 0.7, 0.7, 0.3, 0.2\}$$
$$Tp=\{0.7, 0.7, 0.7, 0.7, 0.7, 0.7\} \qquad (6)$$

As shown in Expression (6), the scattered radiation transmittance Ts and the primary radiation transmittance Tp have the same value in a high frequency band (r=1 to 4) and the scattered radiation transmittance Ts is lower than the primary radiation transmittance Tp in a low frequency band (r=5 to 6). The reason is that the grid has a higher removal rate in a lower frequency band in which the frequency component of the scattered radiation is dominant and the dependence of the removal rate of the grid for the primary radiation on the frequency is low.

Figure 4:
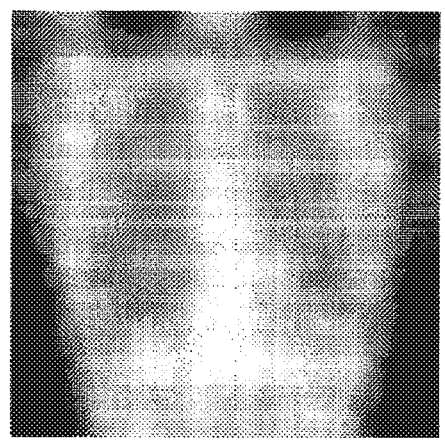
FIG. 4 is a diagram illustrating a scattered radiation content distribution in a radiographic image of the chest.
Figure 5:
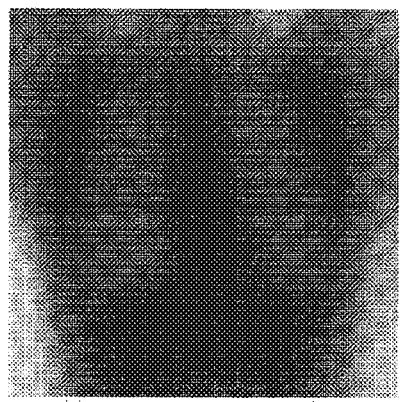
FIG. 5 is a diagram illustrating a conversion coefficient which is calculated in a case in which the scattered radiation content distribution illustrated in FIG. 4 is shown.

FIG. 4 is a diagram illustrating a scattered radiation content distribution S(x, y) in a radiographic image of the chest. In FIG. 4, as the scattered radiation content distribution S(x, y) becomes higher, brightness at each pixel position becomes higher. As can be seen from FIG. 4, in the image of the chest, the content of scattered radiations in the mediastinal part and around the lung field is high. FIG. 5 illustrates the conversion coefficient which is calculated on the basis of Expressions (4) and (6) in a case in which the scattered radiation content distribution S(x, y) is shown. In FIG. 5, as brightness becomes lower, the value of the conversion coefficient becomes smaller and the pixel value is more significantly reduced. As can be seen from the comparison between FIG. 4 and FIG. 5, the value of the conversion coefficient is small in the mediastinal portion and around the lung field where the content of scattered radiation is high. Therefore, in the processed radiographic image acquired by performing the process shown in Expression (5) using the conversion coefficient calculated in this way, a scattered component is removed according to the type of grid to be used.

The removal processing unit 43 may remove the scattered radiations of the radiographic image as follows. First, similarly to the above, if frequency synthesis is represented by I(x, y)=Σrl(x, y, r), the removal processing unit 43 decomposes the frequency component image I(x, y, r) into a scattered component Ics(x, y, r) and a primary radiation component Icp(x, y, r) on the basis of the scattered radiation content distribution S(x, y), using the following Expression (7).

$$Ics(x,y,r)=S(x,y)\times I(x,y,r)$$
$$Icp(x,y,r)=(1-S(x,y))\times I(x,y,r) \qquad (7)$$

The removal processing unit 43 applies the scattered radiation transmittance Ts(r) and the primary radiation transmittance Tp(r), which are the virtual grid characteristics, to the scattered component Ics(x, y, r) and the primary radiation component Icp(x, y, r), respectively, to perform image conversion, thereby calculating a converted scattered component Ics'(x, y, r) and a converted primary radiation component Icp'(x, y, r), using the following Expression (8).

$$Ics'(x,y,r)=Ics(x,y,r)\times Ts(r)=S(x,y)\times I(x,y,r)\times Ts(r)$$
$$Icp'(x,y,r)=Icp(x,y,r)\times Tp(r)=(1-S(x,y))\times I(x,y,r)\times Tp(r) \qquad (8)$$

Then, the removal processing unit 43 performs frequency synthesis for scattered component Ics'(x, y, r) and the primary radiation component Icp'(x, y, r) to calculate a processed radiographic image I'(x, y), using the following Expression (9).

$$I'(x, y) = \Sigma r\{Ics'(x, y, r) + Icp'(x, y, r)\} \qquad (9)$$
$$= \Sigma r\{S(x, y) \times I(x, y, r) \times Ts(r) +$$
$$(1 - S(x, y)) \times I(x, y, r) \times Tp(r)\}$$
$$= \Sigma r\{I(x, y, r) \times (S(x, y) \times Ts(r) +$$
$$(1 - S(x, y)) \times Tp(r))\}$$

The image processing unit 36 performs image processing, such as a noise removal process of removing noise, a gradation process, and a frequency process, for the radiographic image subjected to the grid stripe removal process, the radiographic image subjected to the scattered radiation removal process, and the radiographic image before the scattered radiation removal process and acquires a processed radiographic image.

The display control unit 37 displays the radiographic image subjected to the grid stripe removal process on the display unit 8 in a case in which a grid stripe is detected and displays the radiographic image subjected to the scattered radiation removal process and the radiographic image before the scattered radiation removal process on the display unit 8 in a case in which a grid stripe is not detected. Image processing is performed for the radiographic image subjected to the grid stripe removal process, the radiographic image subjected to the scattered radiation removal process, and the radiographic image before the scattered radiation removal process and the processed radiographic images are displayed on the display unit 8. In the following description, the radiographic image subjected to the grid stripe removal process and the image processing is referred to as a radiographic image G1, the radiographic image subjected to the scattered radiation removal process and the image processing is referred to as a radiographic image G2, and the radiographic image subjected to only the image processing is referred to as a radiographic image G0.

Figure 6:
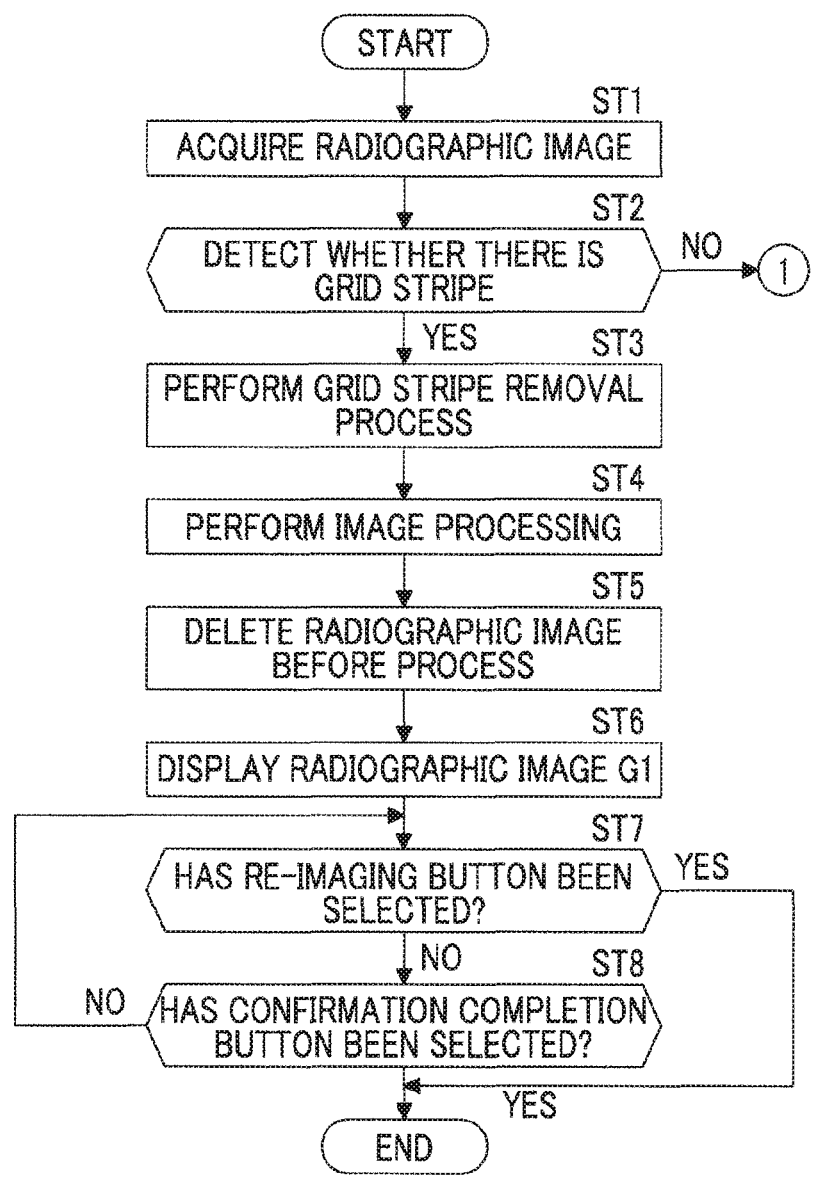
FIG. 6 is a flowchart illustrating a process which is performed in the first embodiment (part 1).
Figure 7:
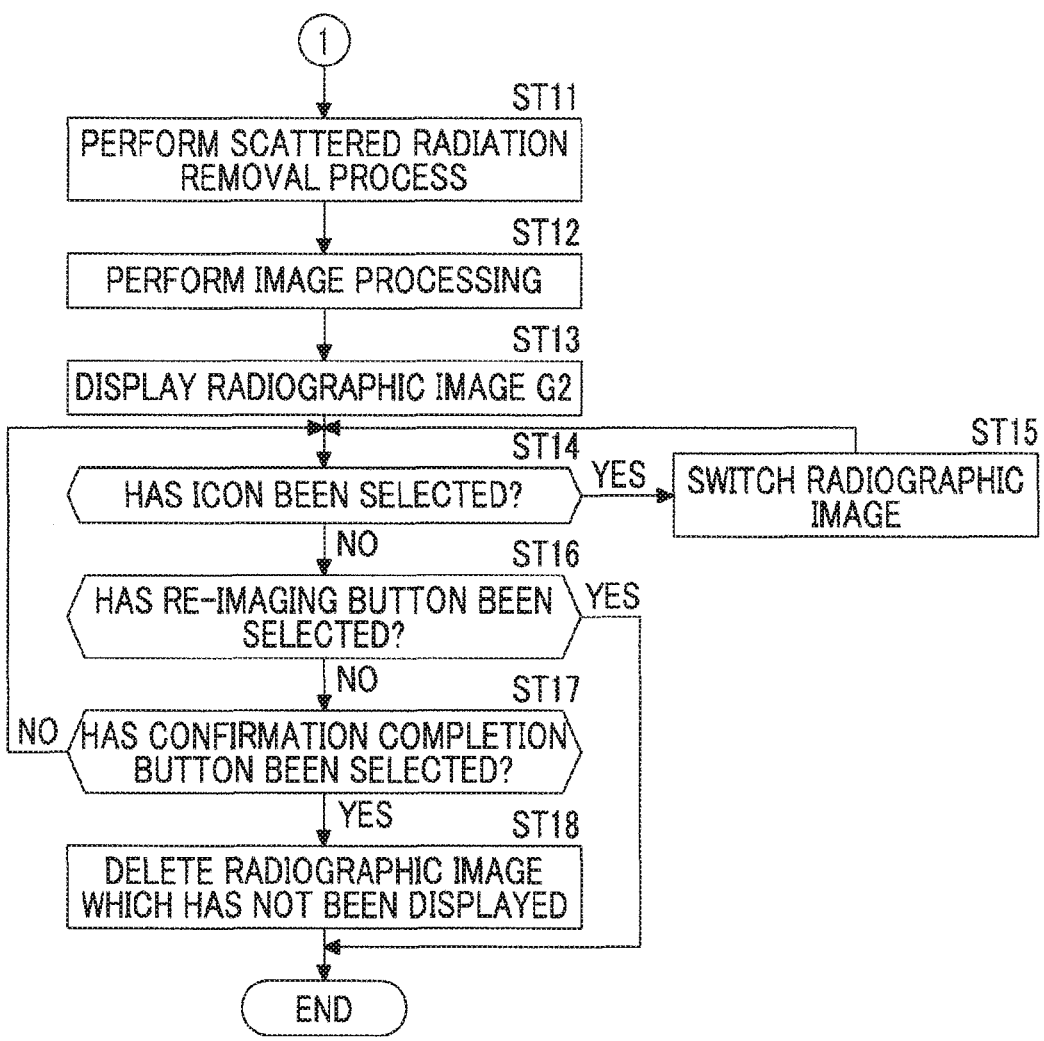
FIG. 7 is a flowchart illustrating the process which is performed in the first embodiment (part 2).

Next, a process which is performed in the first embodiment will be described. FIGS. 6 and 7 are flowcharts illustrating the process which is performed in the first embodiment. When the image acquisition unit 32 acquires a radiographic image from the radiation detectors 4 and 5 (Step ST1), the grid stripe detection unit 33 detects whether a grid stripe is present in the radiographic image (Step ST2). When a grid stripe is detected (Step ST2: Yes), the grid stripe removal unit 34 performs the grid stripe removal process for the radiographic image (Step ST3) and the image processing unit 36 performs image processing for the radiographic image subjected to the grid stripe removal process to generate a processed radiographic image G1 (Step ST4). Then, the control unit 31 deletes the radiographic image before processing (Step ST5). Then, the display control unit 37 displays the radiographic image G1 on the display unit 8 (Step ST6).

Figure 8:
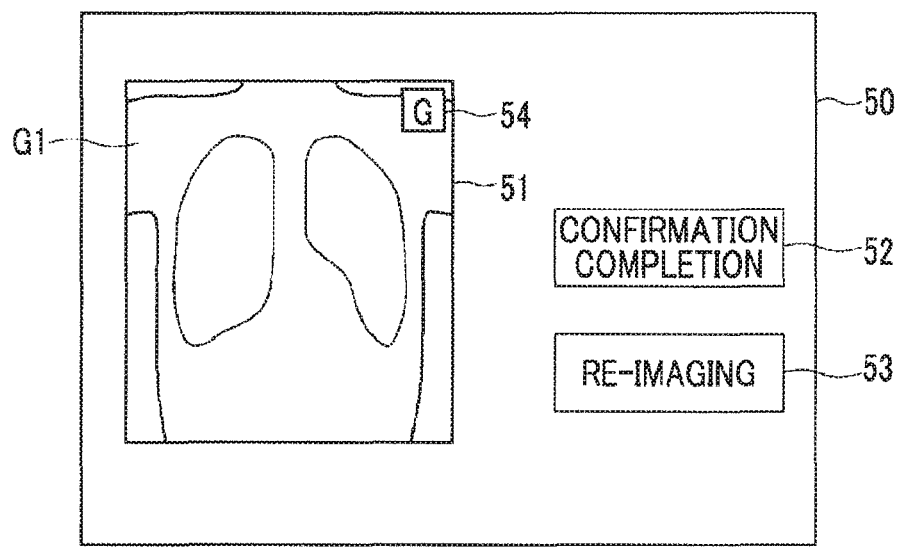
FIG. 8 is a diagram illustrating an example of a confirmation screen.

FIG. 8 is a diagram illustrating a confirmation screen for the radiographic image G1. As illustrated in FIG. 8, an image display region 51 in which a processed radiographic image is displayed, a confirmation completion button 52, and a re-imaging button 53 are displayed on a confirmation screen 50. In addition, the radiographic image G1 and an icon indicating the process which has performed for the radiographic image are displayed in the image display region 51. On the confirmation screen 50 illustrated in FIG. 8, an icon 54 including a letter "G" indicating that the grid stripe removal process has been performed is displayed in the radiographic image G1 displayed on the image display region 51.

Then, the control unit 31 determines whether the re-imaging button 53 has been selected (Step ST7). When the determination result in Step ST7 is "Yes", the control unit 31 ends the process for re-imaging. When the determination result in Step ST7 is "No", the control unit 31 determines whether the confirmation completion button 52 has been selected (Step ST8). When the determination result in Step ST8 is "No", the process returns to Step ST7. On the other hand, when the determination result in Step ST8 is "Yes", the process ends. The processed radiographic image G1 is stored in the storage unit 38 or it is transmitted to a server that is connected to the console 6 through a network and is then stored in the server.

Figure 9:
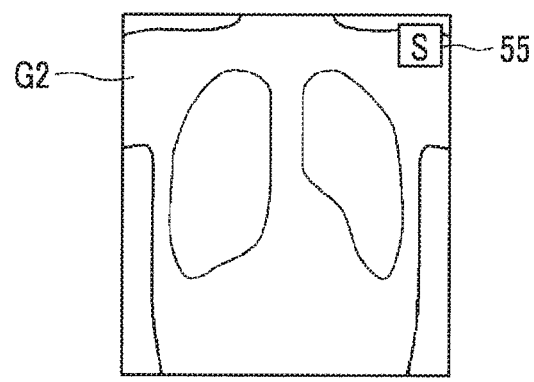
FIG. 9 is a diagram illustrating a radiographic image subjected to a scattered radiation removal process and image processing.

On the other hand, when a grid stripe is not detected (Step ST2: No), the scattered radiation removal unit 35 performs the scattered radiation removal process for the radiographic image (Step ST11). The image processing unit 36 performs image processing for the radiographic image subjected to the scattered radiation removal process and the radiographic image before the scattered radiation removal process to generate processed radiographic images G0 and G2 (Step ST12). Then, the display control unit 37 displays the radiographic image G2 on the display unit 8 (Step ST13). In this case, the radiographic image G2, to which an icon 55 including a letter "S" which indicates that the scattered radiation removal process and image processing have been performed for the radiographic image is given, is displayed in the image display region 51 of the confirmation screen 50, as illustrated in FIG. 9.

Figure 10:
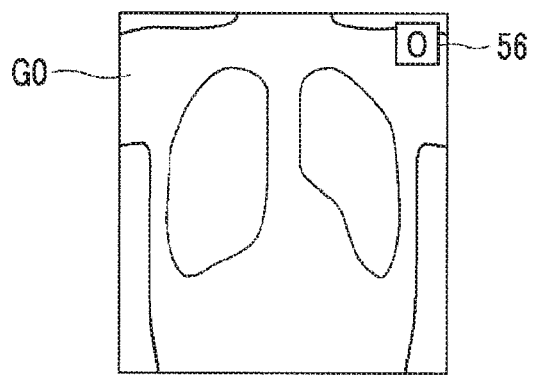
FIG. 10 is a diagram illustrating a radiographic image subjected to only image processing.

The control unit 31 determines whether the icon 55 has been selected (Step ST14). When the determination result in Step ST14 is "Yes", the display control unit 37 switches the radiographic image displayed on the display unit 8 (Step ST15) and the process returns to Step ST14. In this case, instead of the radiographic image G2, the radiographic image G0 subjected to only the image processing is displayed on the display unit 8. As illustrated in FIG. 10, the radiographic image G0, to which an icon 56 including a letter "0" which indicates that only the image processing has been performed for the radiographic image is given, is displayed in the image display region 51 of the confirmation screen 50. In Step ST14, the control unit 31 determines whether the icon 56 has been selected. When the determination result in Step ST14 is "Yes", the control unit 31 displays the radiographic image G2 on the display unit 8 again.

When the determination result in Step ST14 is "No", the control unit 31 determines whether the re-imaging button 53 has been selected (Step ST16). When the determination result in Step ST16 is "Yes", the control unit 31 ends the process for re-imaging. When the determination result in Step ST 16 is "No", the control unit 31 determines whether the confirmation completion button 52 has been selected (Step ST17). When the determination result in Step ST17 is "No", the process returns to Step ST14. On the other hand, when the determination result in Step ST17 is "Yes", the control unit 31 deletes the radiographic image which has not been displayed (Step ST18) and ends the process. That is, when the radiographic image G2 is displayed, the control unit 31 deletes the radiographic image G0. When the radiographic image G0 is displayed, the control unit 31 deletes the radiographic image G2. The processed radiographic image which has not been deleted is stored in the storage unit 38 or it is transmitted to the server that is connected to the console 6 through the network and is then stored in the server.

As such, in the first embodiment, it is detected whether there is a grid stripe. In a case in which a grid stripe is detected, the grid stripe removal process is performed. In a case in which no grid stripe is detected, the scattered radiation removal process is performed. In a case in which a grid stripe is detected, the radiographic image G1 from which the grid stripe has been removed is displayed. In a case in which no grid stripe is detected, the radiographic image G2 subjected to the scattered radiation removal process and the radiographic image G0 before the scattered radiation removal process are displayed. Therefore, an appropriate process corresponding to whether a grid is used during imaging can be performed for the radiographic image even if the operator does not perform any operation. As a result, it is possible to reduce a burden on the operator and to perform the grid stripe removal process and the scattered radiation removal process with high efficiency.

In this embodiment, in a case in which a Bucky grid is used, no grid stripe is detected from a radiographic image and the scattered radiation removal process is performed.

The scattered radiations have been removed from the radiographic image acquired by performing an imaging process using the Bucky grid. Therefore, when the scattered radiation removal process is performed, an image with a large amount of noise which seems to be captured with a very low dose is obtained. According to this embodiment, the radiographic image G2 subjected to the scattered radiation removal process and the radiographic image G0 before the scattered radiation removal process are displayed. Therefore, the operator can check whether the displayed image is an image obtained by performing the scattered radiation removal process for the radiographic image captured using the Bucky grid. In addition, the operator can perform an operation to delete the radiographic image before the scattered radiation removal process. As a result, it is possible to prevent a radiographic image obtained by performing the scattered radiation removal process for the radiographic image which is captured using the Bucky grid from remaining and from being used for diagnosis.

In the first embodiment, in a case in which no grid stripe is detected, when the confirmation completion button 52 is selected, the radiographic image which has not been displayed is deleted. However, both the radiographic images G0 and G2 may be stored. In addition, in a case in which both the radiographic images G0 and G2 are stored, the radiographic image which has not been displayed is deleted after a predetermined period of time has elapsed since the storage.

In the first embodiment, the radiographic images G0 and G2 may be displayed side by side. Then, when an unnecessary radiographic image is selected, the selected radiographic image may be deleted.

Figure 11:
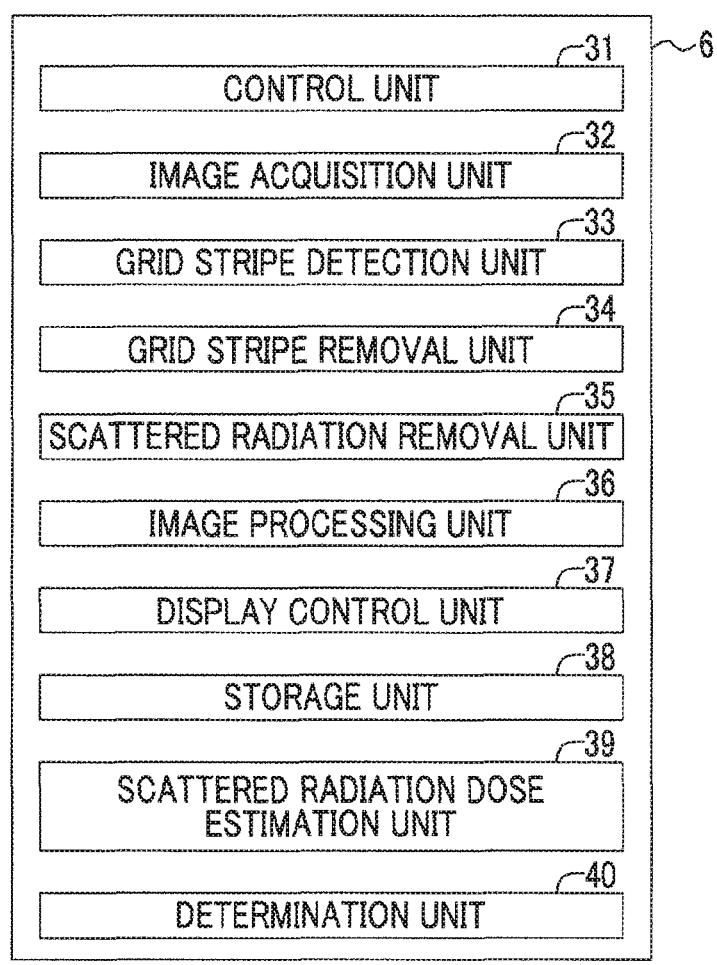
FIG. 11 is a block diagram schematically illustrating the internal structure of a computer of a radiography system in a second embodiment.

Next, a second embodiment of the invention will be described. FIG. 11 is a block diagram schematically illustrating the internal structure of a computer in a radiography system according to the second embodiment of the invention. In FIG. 11, the same components as those in FIG. 2 are denoted by the same reference numerals and the detailed description thereof will not be repeated. The second embodiment differs from the first embodiment except that it includes a scattered radiation dose estimation unit 39 that estimates a scattered radiation dose of a radiographic image in a case in which a grid stripe is not detected from a radiographic image and a determination unit 40 that determines whether a grid has been used on the basis of the estimated scattered radiation dose.

Figure 12:
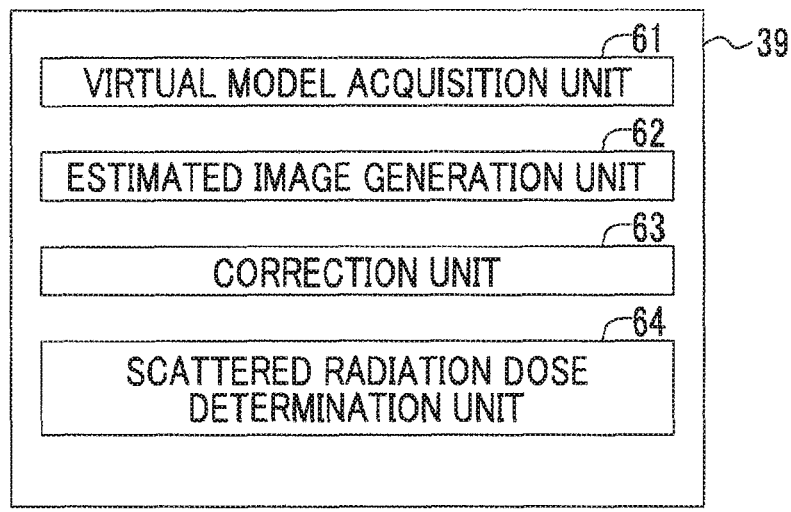
FIG. 12 is a block diagram schematically illustrating the structure of a scattered radiation dose estimation unit.

FIG. 12 is a block diagram schematically illustrating the structure of the scattered radiation dose estimation unit 39. As illustrated in FIG. 12, the scattered radiation dose estimation unit 39 includes a virtual model acquisition unit 61, an estimated image generation unit 62, a correction unit 63, and a scattered radiation dose determination unit 64.

The virtual model acquisition unit 61 acquires a virtual model K of a subject M having an initial body thickness distribution $T_0$ (predetermined body thickness distribution).

The estimated image generation unit 62 generates a composite image of an estimated primary radiation image Ip, which is obtained by estimating a primary radiation image obtained by radiography of the virtual model, and an estimated scattered radiation image Is, which is obtained by estimating a scattered radiation image obtained by radiography of the virtual model, as an estimated image Im which is obtained by estimating a radiographic image obtained by radiography for the subject M, on the basis of the virtual model K.

The correction unit 63 corrects the initial body thickness distribution $T_0$ of the virtual model K such that the difference between the estimated image Im and the radiographic image is reduced, on the basis of the estimated image Im and the radiographic image.

The scattered radiation dose determination unit 64 determines a scattered radiation dose of the radiographic image on the basis of the corrected body thickness distribution $T_{n-1}$ (n is a natural number).

In the second embodiment, the storage unit 38 stores the virtual model K of the subject M having the initial body thickness distribution $T_0(x, y)$. The body thickness means the total thickness of a subject region except for an air region on the path of the emitted radiation.

Figure 13:
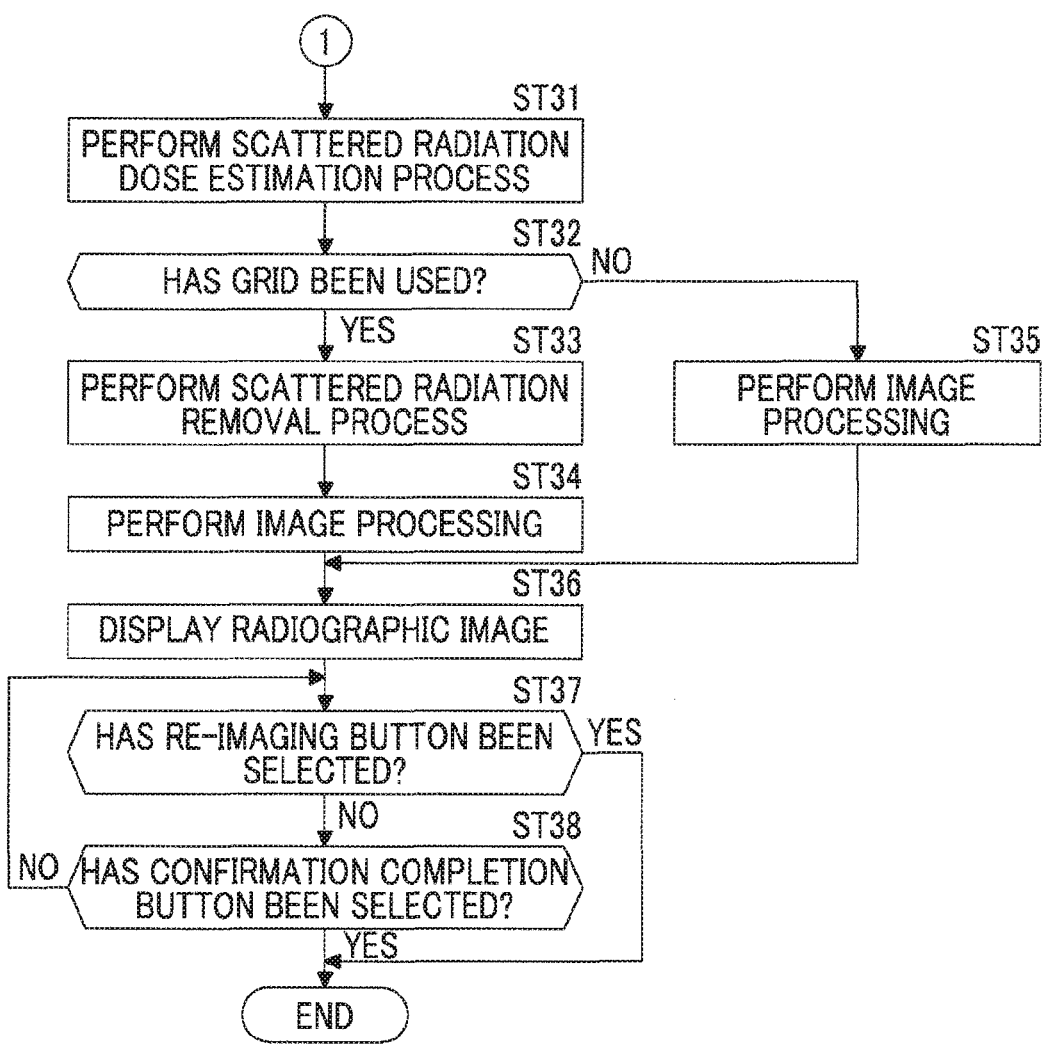
FIG. 13 is a flowchart illustrating a process which is performed in the second embodiment.

Next, a process which is performed in the second embodiment will be described. FIG. 13 is a flowchart illustrating the process performed in the second embodiment. The process illustrated in the flowchart of FIG. 13 is performed in a case in which the determination result in Step ST2 in the first embodiment is "No". Therefore, the flowchart illustrates the process after the determination result in Step ST2 is "No". When the determination result in Step ST2 is "No", the scattered radiation dose estimation unit 39 performs a scattered radiation dose estimation process (Step ST31).

Figure 14:
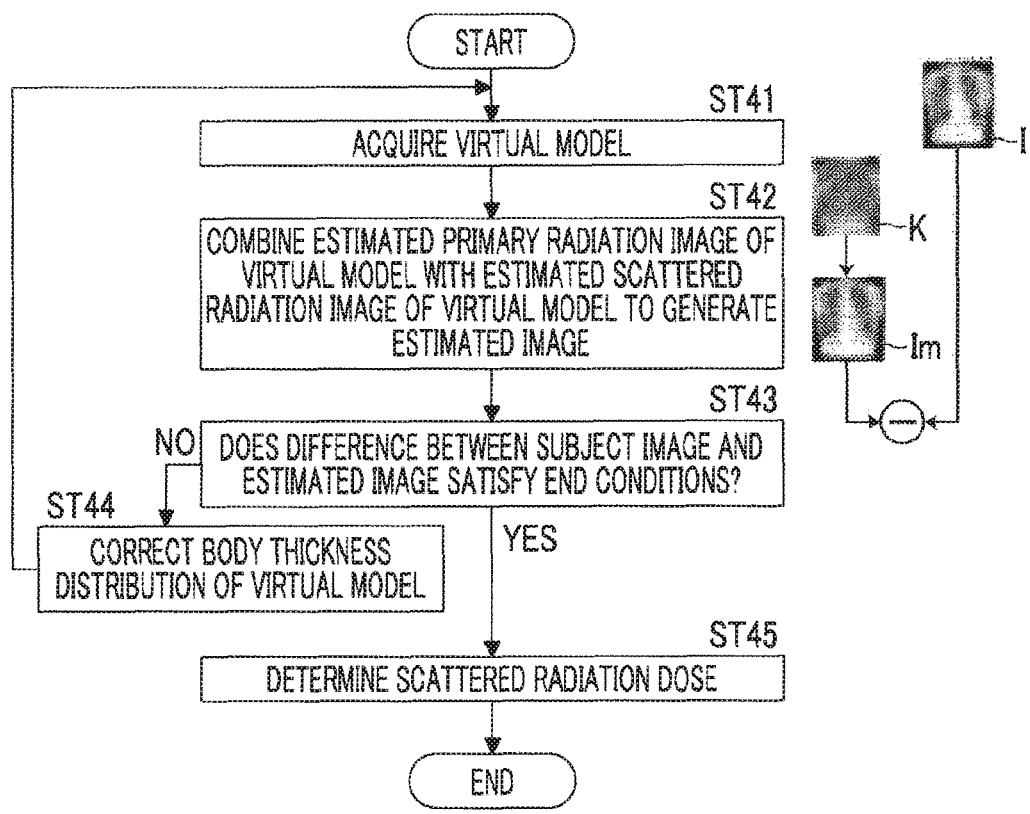
FIG. 14 is a flowchart illustrating a scattered radiation dose estimation process.

FIG. 14 is a flowchart illustrating the scattered radiation dose estimation process. The virtual model acquisition unit 61 of the scattered radiation dose estimation unit 39 acquires the virtual model K of the subject M having the initial body thickness distribution $T_0(x, y)$ from the storage unit 38 (Step ST41). The virtual model K is data which virtually indicates the subject M and in which a body thickness that follows the initial body thickness distribution $T_0(x, y)$ is associated with each position on an x-y plane. In addition, structures (here, anatomic structures such as a lung field, a bone, and an organ) included in the virtual model K, the arrangement of the structures, and characteristic information indicating, for example, the characteristics of the structures with respect to radiation are set on the basis of the arrangement and composition of anatomic structures, such as the lung field of the chest and abdomen of a comparative subject and the bones.

Figure 15:
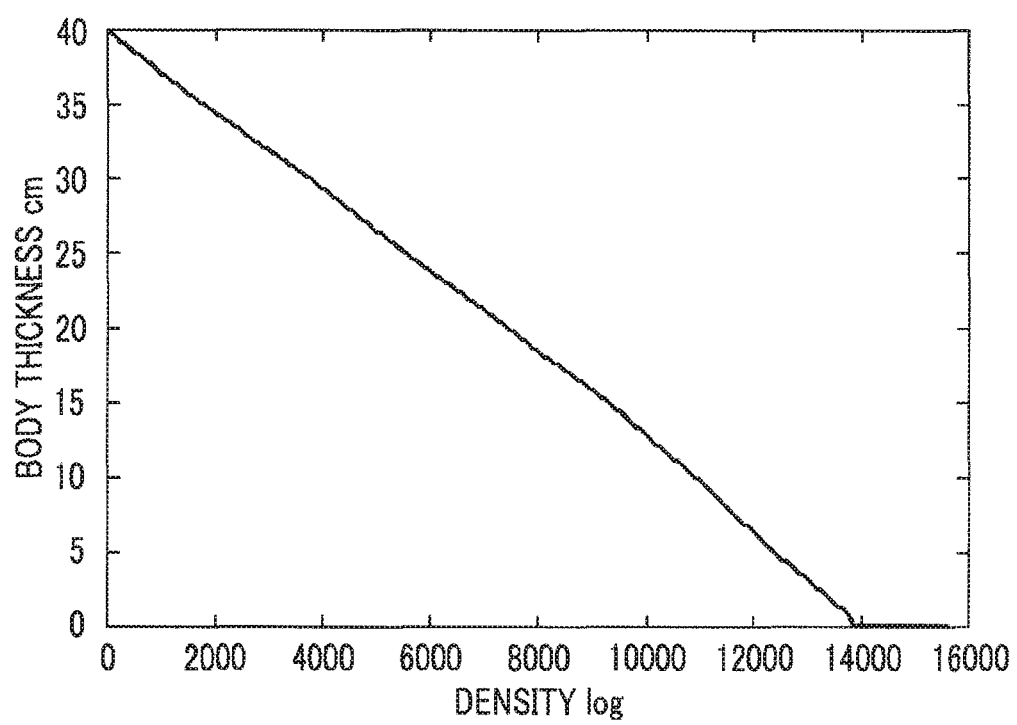
FIG. 15 is a diagram illustrating an example of a body thickness distribution correspondence table.

The virtual model K may have any initial body thickness distribution $T_0(x, y)$. However, in this embodiment, the initial body thickness distribution $T_0$ is generated and acquired by the virtual model acquisition unit 61. The virtual model acquisition unit 61 acquires imaging conditions, such as the radiation dose of the subject M, a tube voltage, and an SID, and acquires a table in which the pixel value corresponding to the imaging conditions of the subject M is associated with the body thickness from the storage unit 38. FIG. 15 illustrates an example of the table in which the pixel value is associated with the body thickness. Then, the virtual model acquisition unit 61 specifies the body thickness corresponding to the value of each pixel in the radiographic image of the subject M on the basis of the table illustrated in FIG. 15 to acquire the body thickness distribution of the radiographic image. Then, the virtual model acquisition unit 61 acquires the body thickness distribution of the radiographic image as the initial body thickness distribution $T_0$ (predetermined body thickness distribution) of the virtual model K. The initial body thickness distribution $T_0$ may be generated during the process of acquiring the virtual model K as in this embodiment, or may be set before the process of acquiring the virtual model K in advance. The above-mentioned process is represented by the following Expression (11). In addition, I(x, y) indicates the value of each pixel in a radiographic image and $T_0(x, y)$ indicates an initial body thickness distribution at each pixel position.

$$T_0(x,y)=LUT(I(x,y)) \qquad (11)$$

Figure 16:
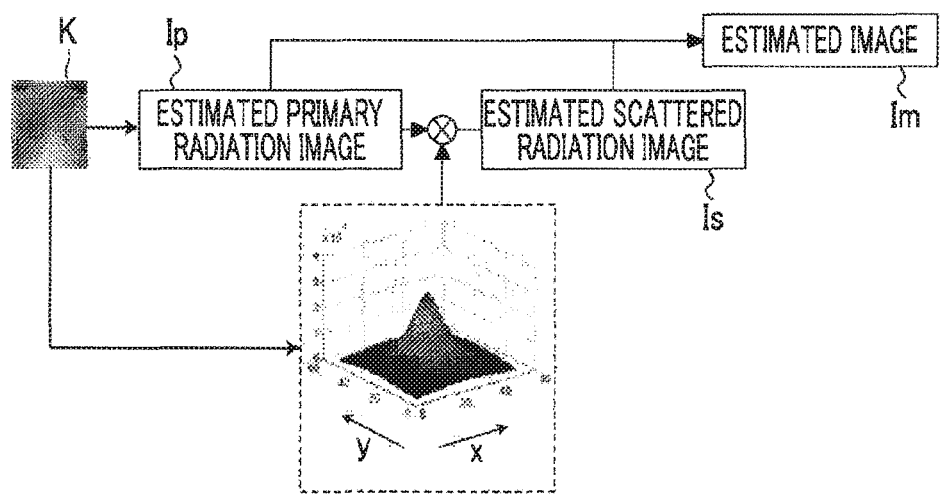
FIG. 16 is a diagram illustrating an example of an estimated image generation method.
Figure 17:
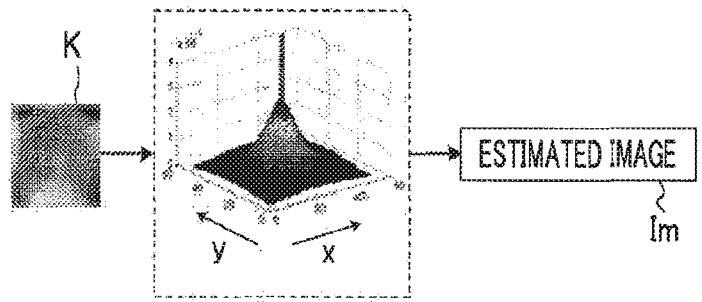
FIG. 17 is a diagram illustrating another example of the estimated image generation method.

Then, the estimated image generation unit 62 combines an estimated primary radiation image Ip, which is obtained in a case in which the image of the virtual model K is captured under the same imaging conditions as the radiographic image, and an estimated scattered radiation image Is, which is obtained in a case in which the image of the virtual model K is captured under the same imaging conditions as the radiographic image, to generate an estimated image Im (Step ST42). FIGS. 16 and 17 are diagrams illustrating a method for generating the estimated image Im.

As illustrated in FIG. 16, the estimated image generation unit 62 generates the estimated primary radiation image Ip, which is obtained in a case in which the image of the virtual model K is captured under the same imaging conditions as the radiographic image, according to the following Expression (12), and generates the estimated scattered radiation image Is using the generated estimated primary radiation image Ip, according to the following Expression (13). Then, the estimated image generation unit 62 combines the estimated primary radiation image Ip and the estimated scattered radiation image Is to generate the estimated image Im, as shown in the following Expression (14) (Step ST42). When the estimated primary radiation image Ip and the estimated scattered radiation image Is are generated first, the initial body thickness distribution $T_0(x, y)$ is used in Estimation Expressions (12) and (13) (n is 1 in Expressions (12) and (13)).

$$I_p(x, y) = I_o(x, y) \times \exp(-T_{n-1}(x, y) \times \mu) \tag{12}$$

$$I_s(x, y) = \sum_{x', y'} I_p(x', y') K_s(x, y, T_{n-1}(x', y'), \theta_{x', y'}) \tag{13}$$

$$I_m(x, y) = I_p(x, y) + I_s(x, y) \tag{14}$$

Here, (x, y) is the coordinates of a pixel position in a radiographic image, Ip(x, y) is an estimated primary radiation image at the pixel position (x, y), Is(x, y) is an estimated scattered radiation image at the pixel position (x, y), Io(x, y) is a dose at the pixel position (x, y), Im(x, y) is an estimated image at the pixel position (x, y), t is a linear attenuation coefficient of the subject, and Ks(x, y, Tn(x', y'), θx', y') is a convolution kernel indicating a point spread function corresponding to the thickness of the subject at the pixel position (x, y). The dose Io(x, y) is a radiation dose which is detected by the radiation detectors 4 and 5 on the assumption that no subject is present and varies depending on the distance (SID) between the radiation source 2 and the detection surfaces of the radiation detectors 4 and 5, a tube voltage, and an mAs value. In addition, θx', y' indicates a parameter which is specified by the imaging conditions, such as the tube voltage, or the characteristic information of the virtual model K.

In addition, the estimated image Im may be an image which is estimated to be obtained in a case in which the radiographic image of the virtual model K is captured and may be any image which is substantially regarded as a composite image of the estimated primary radiation image Ip and the estimated scattered radiation image Is. For example, as illustrated in FIG. 17, the estimated image Im may be generated by the convolution integral of the kernel combining a primary radiation component and a scattered component, using the following Expression (15), instead of Expressions (12) to (14). Here, Kp+s(x, y, Tn−1(x', y'), θx', y') is a kernel indicating a point spread function that combines the primary radiation component and the scattered component. In addition, any model function may be used as long as it can generate an estimated image obtained by combining the estimated primary radiation image and the estimated scattered radiation image from the image obtained by radiography.

In addition, Ks(x, y, Tn(x', y'), θx', y') and Kp+s(x, y, Tn−1(x', y'), θx', y') can be experimentally calculated according to, for example, imaging conditions.

In this embodiment, the kernels Ks(x, y, Tn(x', y'), θx', y') and Kp+s(x, y, Tn−1(x', y'), θx', y') may be calculated on the basis of the imaging conditions during imaging. A table in which various imaging conditions and the kernels Ks(x, y, Tn(x', y'), θx', y') and Kp+s(x, y, Tn−1(x', y'), θx', y') are associated with each other is stored in the storage unit 38 and the kernels Ks(x, y, Tn(x', y'), θx', y') and Kp+s(x, y, Tn−1(x', y'), θx', y') are calculated on the basis of irradiation field information, subject information, and imaging conditions during imaging, with reference to the table.

$$I_m(x, y) = \sum_{x', y'} K_{p+s}(x, y, T_{n-1}(x', y'), \theta_{x', y'}) \tag{15}$$

The next process will be described with reference to the flowchart illustrated in FIG. 14. Then, the scattered radiation dose determination unit 64 determines whether the difference between the radiographic image and the estimated image Im satisfies end conditions (Step ST43). Here, an error value $V_{error}$, indicating the difference between the radiographic image and the estimated image Im is defined as shown in the following Expressions (16) and (17). It is determined whether the error value $V_{error}$ is equal to or less than a threshold value as the end conditions. As shown in Expression (17), the sum of the squares of each pixel value of a difference image Id which is obtained by subtracting the estimated image Im from the radiographic image is defined as an error function $f_{error}$. In addition, any determination method may be used as long as it can determine whether or not the difference between the radiographic image and the estimated image Im is small enough to be allowable, as the end conditions.

$$V_{error} = f_{error}(I_m(x, y), I(x, y)) \tag{16}$$

$$f_{error}(I_m(x, y), I(x, y)) = \sum_{x, y} (I_m(x, y) - I(x, y))^2 \tag{17}$$

However, the invention is not limited to the above-mentioned example. For example, the error function $f_{error}$, can be defined by any method which can indicate the difference between the radiographic image and the estimated image Im. For example, as shown in the following Expression (18), the sum of the absolute values of each pixel value of the differential image Id obtained by subtracting the estimated image Im from the radiographic image may be defined as the error function $f_{error}$.

$$f_{error}(I_m(x, y), I(x, y)) = \sum_{x, y} |I_m(x, y) - I(x, y)| \tag{18}$$

In a case in which the error value $V_{error}$ does not satisfy the end conditions (Step ST43; No), the scattered radiation dose determination unit 64 performs a correction process of correcting a body thickness distribution Tn−1 (the initial body thickness distribution $T_0$ in a case in which n is 1) (Step ST44).

Any method which can acquire the correction value of each position in the body thickness distribution Tn−1 such that the difference between the radiographic image and the estimated image Im is reduced can be applied in order to perform the process of correcting the body thickness distribution Tn−1. In this embodiment, a process is performed which changes the body thickness distribution Tn−1 of the virtual model K for each partial region including one or more pixels in the virtual model K to calculate the body thickness of the partial region where the difference between the estimated image Im and the radiographic image is small. Then, the body thickness distribution of the virtual model is corrected using the calculated body thickness of each partial region.

Specifically, in this embodiment, it is assumed that the correction value of the body thickness with the body thickness distribution Tn−1 is calculated using the steepest descent method. It is possible to minimize the output value of the error function $f_{error}$ by repeatedly calculating dTn−1 (x, y) on the basis of the primary partial differential (gradient) of the error function $f_{error}$, while changing only the body thickness at one specific coordinate point in Tn−1(x, y) among the pixels of the virtual model K, using the following Expressions (19) and (20). Then, the body thickness at one specific coordinate point when the output value of the error function $f_{error}$ is minimized is determined as the correction value of the body thickness at the specific coordinate point. For the other pixels, similarly, the correction value of each body thickness is calculated and the body thickness distribution of each pixel is corrected. In this way, a corrected body thickness distribution Tn is acquired.

$$T_n(x, y) = T_{n-1}(x, y) - \alpha dT_{n-1}(x, y) = T_{n-1}(x, y) - \alpha \frac{d}{dT_{n-1}(x, y)} f_{error} \quad (19)$$

$$\frac{d}{dT_{n-1}(x, y)} f_{error} = \sum_{x',y'} (I_m(x', y') - I(x', y')) \frac{d}{dT_{n-1}(x, y)} K_{p+s}(x', y', T_{n-1}(x, y), \theta_{x,y}) \quad (20)$$

$$\frac{d}{dT_{n-1}(x, y)} K_{p+s}(x', y', T_{n-1}(x, y), \theta_{x,y}) = K_{p+s}(x', y', T_{n-1}(x, y) + dt, \theta_{x,y}) - K_{p+s}(x', y', T_{n-1}(x, y), \theta_{x,y}) \quad (21)$$

However, in Expression (19), at is an update coefficient which is a parameter indicating the update speed of the body thickness. As an example of a method for calculating a differential value portion of Kp+s shown in Expression (20), for example, a value change when a very small value dt is added to Tn−1(x, y) can be calculated by Expression (21) and can be used as the value of Kp+s in the Expression (20). In Expressions (11) to (21), the same components are denoted by the same reference numerals and the description thereof will not be repeated. Any optimization method can be applied as long as it can minimize the error value $V_{error}$ indicating the difference between the radiographic image and the estimated image Im. For example, a simplex method, the steepest descent method, or a conjugate gradient method can be used.

When the corrected body thickness distribution Tn is acquired, the scattered radiation dose determination unit 64 increases the value of n by 1 to update the value of n (n=n+1) and the virtual model acquisition unit 61 acquires the corrected body thickness distribution Tn (Step ST41). Then, the estimated image generation unit 62 and the scattered radiation dose determination unit 64 perform the process from Step ST41 to Step ST43 for the acquired body thickness distribution Tn, using the same method as described above. Then, similarly, the process of correcting the body thickness distribution Tn (Step ST44), the process of acquiring the virtual model K having the corrected body thickness distribution Tn (Step ST41), the process of generating a new estimated image Im using the body thickness distribution Tn (Step ST42), and the process of determining whether the difference between a newly generated estimated image Im and the radiographic image satisfies the end conditions (Step ST43) are repeatedly performed until the error value $V_{error}$ indicating the difference between the radiographic image and the estimated image Im satisfies the end conditions.

On the other hand, if it is determined that the error value $V_{error}$ satisfies the end conditions (Step ST43: Yes), the scattered radiation dose determination unit 64 determines the body thickness distribution Tn which is used for the error value $V_{error}$ when the end conditions are satisfied as the body thickness distribution Tk of the radiographic image, determines the representative value of the estimated scattered radiation image Is generated by the estimated image generation unit 62 as the scattered radiation dose of the radiographic image when the body thickness distribution Tk is obtained, and ends the scattered radiation dose estimation process (Step ST45). Here, various values, such as the mean, variance, median, maximum value, and mode of the pixel values of the estimated scattered radiation image Is, can be used as the representative value of the estimated scattered radiation image Is.

The scattered radiation dose estimation process is not limited to the above-mentioned method. Any method can be used which is based on the fact that a large amount of scattered radiation is generated at the boundary between a subject region and a direct radiation region in which no subject is present in a radiographic image. For example, a method can be used which performs a subject recognition process for a radiographic image, calculates the variance of pixel values in the vicinity of the boundary of the recognized subject, and uses the variance as the scattered radiation dose.

Returning to FIG. 13, following the scattered radiation dose estimation process, the determination unit 40 determines whether the scattered radiation dose is greater than a predetermined threshold value Th1 and determines whether the radiographic image has been acquired using the grid (Step ST32). In a case in which the scattered radiation dose is greater than the threshold value Th1, it is determined that radiographic image has been acquired, without using the grid, since the acquired radiographic image includes a large amount of scattered radiation. Therefore, the determination result in Step ST32 is "Yes". The scattered radiation removal unit 35 performs the scattered radiation removal process for the radiographic image (Step ST33) and the image processing unit 36 performs image processing for the radiographic image subjected to the scattered radiation removal process to generate a processed radiographic image G2 (Step ST34). In this case, the radiographic image before the process may be deleted or may not be deleted.

On the other hand, in a case in which the scattered radiation dose is equal to or less than the threshold value Th1, it is determined that radiographic image has been acquired, using the Bucky grid, since the acquired radiographic image has a small scattered radiation dose and does not include a grid stripe. Therefore, the determination result in Step ST32 is "No". The image processing unit 36 performs only image processing for the radiographic image to generate a processed radiographic image G0 (Step ST35).

Then, the display control unit 37 displays the radiographic image G2 or the radiographic image G0 on the display unit 8 (Step ST36). In a case in which the radiographic image G2 is displayed, the icon 55 including the letter "S" which indicates that the scattered radiation removal process and image processing have been performed for the radiographic image is given to the radiographic image G2, as illustrated in FIG. 9. In a case in which the radiographic image G0 is displayed, the icon 56 including the letter "O" which indicates that only image processing has been performed for the radiographic image is given to the radiographic image G0, as illustrated in FIG. 10.

Then, the control unit 31 determines whether the re-imaging button 53 has been selected (Step ST37). When the determination result in Step ST37 is "Yes", the control unit 31 ends the process for re-imaging. When the determination result in Step ST37 is "No", the control unit 31 determines whether the confirmation completion button 52 has been selected (Step ST38). When the determination result in Step ST38 is "No", the process returns to Step ST37. On the other hand, when the determination result in Step ST38 is "Yes", the process ends. The processed radiographic image is stored in the storage unit 38 or it is transmitted to the server that is connected to the console 6 through the network and is then stored in the server.

As such, in the second embodiment, in a case in which no grid stripe is detected, the scattered radiation dose of the radiographic image is estimated and it is determined whether a grid has been used on the basis of the scattered radiation dose. In a case in which it is determined that the grid has not been used, the scattered radiation removal process is performed. Therefore, in a case in which the scattered radiation dose included in the radiographic image is small as in a case in which the Bucky grid is used, the scattered radiation removal process is not performed. As a result, it is possible to prevent the scattered radiation removal process from being performed for the radiographic image which is captured using the Bucky grid.

Figure 18:
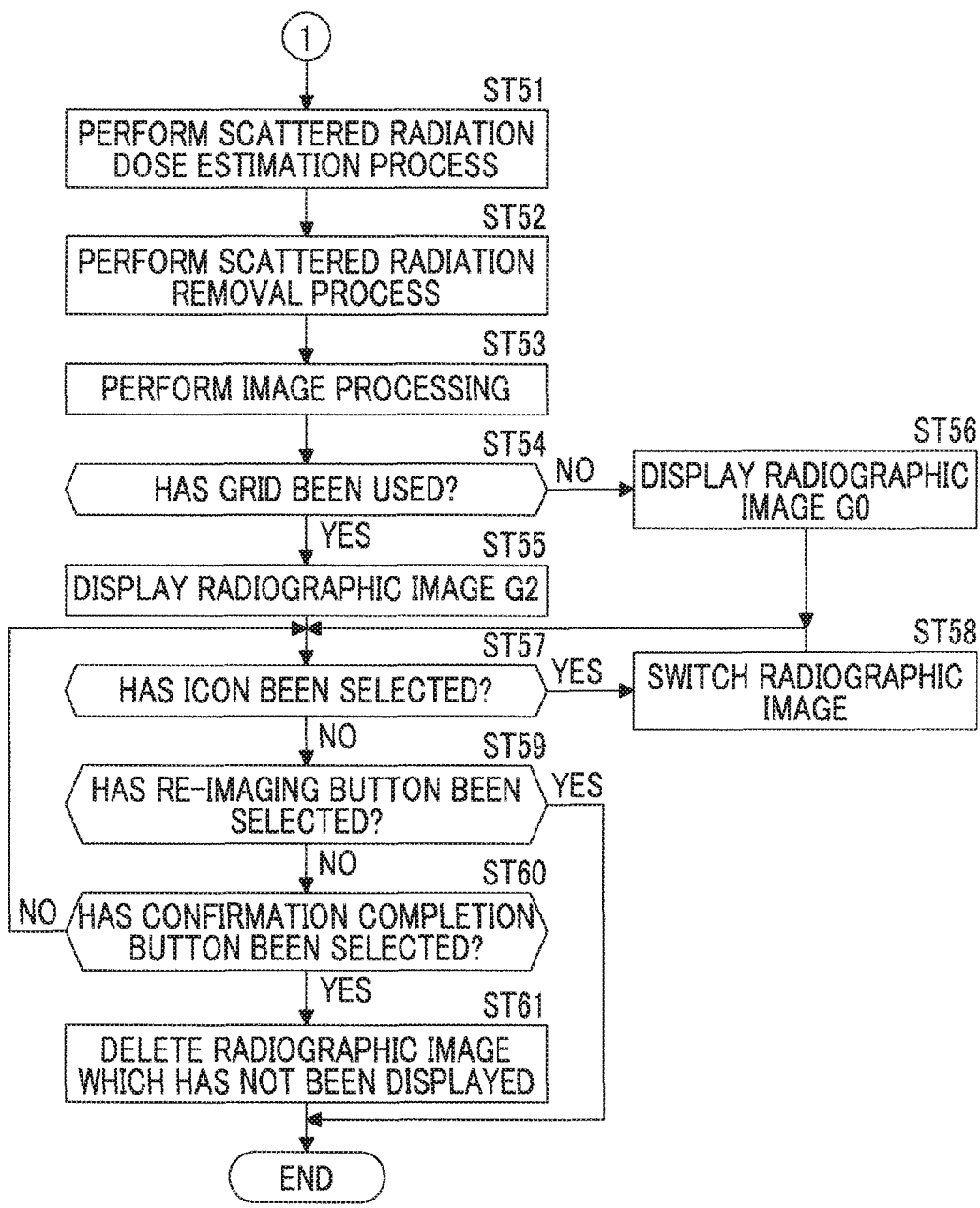
FIG. 18 is a flowchart illustrating a process which is performed in a third embodiment.

Next, a third embodiment of the invention will be described. The third embodiment is similar to the second embodiment except for only the process to be performed. In this embodiment, the detailed description of a structure will be omitted. FIG. 18 is a flowchart illustrating the process performed in the third embodiment. The process illustrated in the flowchart of FIG. 18 is performed in a case in which the determination result in Step ST2 in the first embodiment is "No". Therefore, the flowchart illustrates the process after the determination result in Step ST2 is "No". When the determination result in Step ST2 is "No", the scattered radiation dose estimation unit 39 performs a scattered radiation dose estimation process (Step ST51).

Then, the scattered radiation removal unit 35 performs a scattered radiation removal process for the radiographic image (Step ST52) and the image processing unit 36 performs image processing for the radiographic image subjected to the scattered radiation removal process and the radiographic image before the process to generate processed radiographic images G0 and G2 (Step STS3). Then, the determination unit 40 determines whether a scattered radiation dose is greater than a predetermined threshold value Th1 and determines whether the radiographic image has been acquired using the grid (Step ST54). In a case in which the scattered radiation dose is greater than the threshold value Th1, it is determined that radiographic image has been acquired, without using the grid, since the acquired radiographic image includes a large amount of scattered radiation. Therefore, the determination result in Step ST54 is "Yes" and the display control unit 37 displays the radiographic image G2 on the display unit 8 (Step ST55). In this case, the icon 55 including the letter "S" which indicates that the scattered radiation removal process and image processing have been performed for the radiographic image is given to the radiographic image G2, as illustrated in FIG. 9.

In a case in which the scattered radiation dose is equal to or less than the threshold value Th1, it is determined that the radiographic image has been acquired, using the Bucky grid, since the acquired radiographic image has a small amount of scattered radiation and does not include a grid stripe. Therefore, the determination result in Step ST54 is "No" and the display control unit 37 displays the radiographic image G0 on the display unit 8 (Step ST56). In this case, the icon 56 including the letter "O" which indicates that only image processing has been performed for the radiographic image is given to the radiographic image G0, as illustrated in FIG. 10.

The control unit 31 determines whether an icon has been selected (Step ST57). When the determination result in Step ST57 is "Yes", the display control unit 37 switches the radiographic image displayed on the display unit 8 (Step ST58) and the process returns to Step ST57.

When the determination result in Step ST57 is "No", the control unit 31 determines whether the re-imaging button 53 has been selected (Step ST59). When the determination result in Step ST59 is "Yes", the control unit 31 ends the process for re-imaging. When the determination result in Step ST59 is "No", the control unit 31 determines whether the confirmation completion button 52 has been selected (Step ST60). When the determination result in Step ST60 is "No", the process returns to Step ST57. When the determination result in Step ST60 is "Yes", the control unit 31 deletes the radiographic image which has not been displayed (Step ST61) and ends the process. That is, when the radiographic image G2 is displayed, the radiographic image G0 is deleted. When the radiographic image G0 is displayed, the radiographic image G2 is deleted. The processed radiographic image which has not been deleted is stored in the storage unit 38 or it is transmitted to the server that is connected to the console 6 through the network and is then stored in the server.

As such, in the third embodiment, the scattered radiation dose of the radiographic image is estimated and it is determined whether a grid has been used on the basis of the scattered radiation dose. Then, of the radiographic image subjected to the scattered radiation removal process and the radiographic image before the scattered radiation removal process, the radiographic image to be displayed is determined on the basis of the determination result. Therefore, in a case in which the scattered radiation dose included in the radiographic image is small as in a case in which the Bucky grid is used, the radiographic image which has not been subjected to the scattered radiation removal process can be displayed first.

In the above-described embodiments, two radiation detectors 4 and 5 are used to perform an imaging processing without using a grid, an imaging process using a stationary grid, and an imaging process using the Bucky grid. However, only one radiation detector may be used to perform the imaging processing without using a grid, the imaging process using a stationary grid, and the imaging process using the Bucky grid. In this case, both the stationary grid and the Bucky grid are detached from the radiation detector and are freely provided.

In the above-described embodiments, the scattered radiation removal process is performed for the radiographic image from which no grid stripe has been detected. However, the scattered radiation removal process may be performed for the radiographic image from which a grid stripe has been detected. In this case, the grid stripe removal process and the scattered radiation removal process are sequentially performed for the radiographic image.

The above-mentioned processes make it possible to virtually acquire a radiographic image that seems to be captured, using a grid having a grid ratio of 10:1, which is different from the grid used, on the basis of the radiographic image which is captured using a grid having a grid ratio of 3:1. Specifically, the following method may be used. A table in which the scattered radiation transmittance Ts and the primary radiation transmittance Tp for each frequency band, which are represented by Expression (6), are associated with grid information during imaging and the grid information of the grid that is desired to be virtually used is experimentally created in advance and is then stored in the storage unit 38. Then, grid information indicating the type of grid used during imaging is acquired and the scattered radiation transmittance Ts and the primary radiation transmittance Tp are acquired with reference to the table, on the basis of the acquired grid information and the grid information of the grid that is desired to be virtually used. Then, the scattered radiation removal process is performed. Alternatively, grid information may be acquired from the input unit 9. For example, as described in JP2003-260053A, projections corresponding to the type of grid may be formed on a grid and then detected to acquire grid information.

There is a case in which time-dependent comparison and observation is performed, using the previous radiographic images, in order to diagnose the healing state or progress state of a disease. In a case in which a radiographic image (referred to as a first radiographic image) which is captured without using a scattered radiation removal grid is compared with a radiographic image (referred to as a second radiographic image) which is captured using the scattered radiation removal grid, it is preferable to correct the conditions of the scattered radiation removal process according to this embodiment, on the basis of the processing conditions when a process of removing a stripe pattern caused by the grid is performed for the first radiographic image such that the first and second radiographic images have the same image quality.

In the above-described embodiments, the scattered radiation removal process is performed, using the radiographic image acquired by the imaging device 10 which captures the radiographic image of the subject using the radiation detectors 4 and 5. However, the invention can be applied to the structures disclosed in JP1996-266529A (JP-H08-266529A) and JP1997-24039A (JP-H09-24039A) in which the radiographic image information of the subject is stored and recorded on a storage phosphor sheet as a radiation detector and the radiographic image is photoelectrically read and acquired from the storage phosphor sheet and is then used.

What is claimed is:
1. A radiographic image processing device comprising:
an image acquisition unit for acquiring a radiographic image which is captured by irradiating a subject with radiation;
a grid stripe detection unit for detecting whether a grid stripe, which is a stripe pattern caused by a grid used during imaging, is present in the radiographic image;
a grid stripe removal unit for performing a grid stripe removal process for the radiographic image in a case in which the grid stripe is detected;
a scattered radiation removal unit for performing a scattered radiation removal process of removing a scattered component included in the radiation that is transmitted through the subject during imaging from the radiographic image in a case in which the grid stripe is not detected; and
a display control unit for displaying a radiographic image subjected to the grid stripe removal process on a display unit in the case in which the grid stripe is detected and displaying a radiographic image subjected to the scattered radiation removal process and a radiographic image before the scattered radiation removal process on the display unit in the case in which the grid stripe is not detected.

2. The radiographic image processing device according to claim 1, further comprising:
a control unit for deleting the radiographic image before the scattered radiation removal process in response to an operation of an operator in the case in which the grid stripe is not detected.

3. The radiographic image processing device according to claim 2,
wherein the operation of the operator is an image decision operation which is performed after the radiographic image is checked.

4. The radiographic image processing device according to claim 1, further comprising:
a storage unit for storing the radiographic image subjected to the scattered radiation removal process and the radiographic image before the scattered radiation removal process in the case in which the grid stripe is not detected and deleting the radiographic image before the scattered radiation removal process after a predetermined period of time has elapsed.

5. The radiographic image processing device according to claim 1, further comprising:
a scattered radiation dose estimation unit for estimating a scattered radiation dose of the radiographic image in the case in which the grid stripe is not detected, and
a determination unit for determining whether the grid has been used on the basis of the scattered radiation dose,
wherein the scattered radiation removal processing unit performs the scattered radiation removal process in a case in which it is determined that the grid has not been used.

6. The radiographic image processing device according to claim 1, further comprising:
a scattered radiation dose estimation unit for estimating a scattered radiation dose of the radiographic image in the case in which the grid stripe is not detected; and
a determination unit for determining whether the grid has been used on the basis of the scattered radiation dose,
wherein the display control unit determines which of the radiographic image subjected to the scattered radiation removal process and the radiographic image before the scattered radiation removal process is displayed, on the basis of the determination result.

7. A radiographic image processing method, comprising:
acquiring a radiographic image which is captured by irradiating a subject with radiation;

detecting whether a grid stripe, which is a stripe pattern caused by a grid used during imaging, is present in the radiographic image;

performing a grid stripe removal process for the radiographic image in a case in which the grid stripe is detected;

performing a scattered radiation removal process of removing a scattered component included in the radiation that is transmitted through the subject during imaging from the radiographic image in a case in which the grid stripe is not detected; and displaying a radiographic image subjected to the grid stripe removal process on a display unit in the case in which the grid stripe is detected and displaying a radiographic image subjected to the scattered radiation removal process and a radiographic image before the scattered radiation removal process on the display unit in the case in which the grid stripe is not detected.

8. A non-transitory recording medium having stored therein a radiographic image processing program that causes a computer to perform:

a step of acquiring a radiographic image which is captured by irradiating a subject with radiation;

a step of detecting whether a grid stripe, which is a stripe pattern caused by a grid used during imaging, is present in the radiographic image;

a step of performing a grid stripe removal process for the radiographic image in a case in which the grid stripe is detected;

a step of performing a scattered radiation removal process of removing a scattered component included in the radiation that is transmitted through the subject during imaging from the radiographic image in a case in which the grid stripe is not detected; and a step of displaying a radiographic image subjected to the grid stripe removal process on a display unit in the case in which the grid stripe is detected and displaying a radiographic image subjected to the scattered radiation removal process and a radiographic image before the scattered radiation removal process on the display unit in the case in which the grid stripe is not detected.

* * * * *